(12) United States Patent
Balestrieri et al.

(10) Patent No.: US 12,109,247 B2
(45) Date of Patent: *Oct. 8, 2024

(54) ANTIMICROBIAL PEPTIDES

(71) Applicant: MATERIAS S.r.l., Naples (IT)

(72) Inventors: Marco Balestrieri, Ischia (IT); Gianna Palmieri, Pozzuoli (IT); Gianluca Neglia, Giugliano in Campania (IT); Aniello Anastasio, Naples (IT); Federico Capuano, Salerno (IT); Luca De Stefano, Naples (IT); Luigi Nicolais, Ercolano (IT)

(73) Assignee: MATERIAS S.r.l., Naples (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/932,316

(22) Filed: Sep. 15, 2022

(65) Prior Publication Data
US 2023/0053472 A1 Feb. 23, 2023

Related U.S. Application Data

(63) Continuation of application No. 16/630,615, filed as application No. PCT/EP2018/069304 on Jul. 16, 2018, now Pat. No. 11,478,528.

(30) Foreign Application Priority Data

Jul. 14, 2017 (IT) .......................... 102017000080068

(51) Int. Cl.
| | |
|---|---|
| A61K 38/10 | (2006.01) |
| A01N 37/46 | (2006.01) |
| A01N 63/50 | (2020.01) |
| A61K 47/69 | (2017.01) |
| A61P 31/04 | (2006.01) |

(52) U.S. Cl.
CPC .............. *A61K 38/10* (2013.01); *A01N 37/46* (2013.01); *A01N 63/50* (2020.01); *A61K 47/6929* (2017.08); *A61P 31/04* (2018.01)

(58) Field of Classification Search
CPC .................................................. A61K 38/10
See application file for complete search history.

(56) References Cited

U.S. PATENT DOCUMENTS 11,478,528 B2 * 10/2022 Balestrieri ............. A01N 37/46

FOREIGN PATENT DOCUMENTS

WO   WO-2015038339 A1 * 3/2015 ........... A61K 31/407

OTHER PUBLICATIONS

Taylor et al. "Listeria monocytogenes relA and hpt Mutants Are Impaired in Surface-Attached Growth and Virulence", Journal of Bacteriology, 2002, 621-62 (Year: 2022).*

Jamali et al. "Prevalence, antimicrobial susceptibility and virulotyping of *Listeria* species and *Listeria monocytogenes* isolated from open-air fish markets", BMC Microbiology (2015); pp. 1-7 (Year: 2015).*

Reinhardt et al. "Design and Application of Antimicrobial Peptide Conjugates", International Journal of Molecular Sciences, 2016, 21 pages (Year: 2016).*

Chaudhari et al. "A novel covalent approach to bio-conjugate silver coated single walled carbon nanotubes with antimicrobial peptide", Journal of Nanobiotechnology, 2016, 15 pages (Year: 2016).*

Morales-Avila et al. "Antibacterial Efficacy of Gold and Silver Nanoparticles Functionalized with the Ubiquicidin (28-41) Antimicrobial Peptide", Journal of Nanomaterials, Mar. 25, 2017, 10 pages (Year: 2017).*

Palza ,"Antimicrobial Polymers with Metal Nanoparticles" Int. J. Mol. Sci. 2015, 2099-2116 (Year: 2015).*

Conter et al., "Characterization of antimicrobial resistance of foodborne Listeria monocytogenes", International Journal of Food Microbiology (2009) 497-500.

Costa et al., "Covalent immobilization of antimicrobial peptides (AMPs) onto biomaterial surfaces", Acta Biomaterialia, 2011, 1431-1440.

De La Fuente-Nunez C et A.L., "Broad-spectrum anti-biofilm peptide that targets a cellular stress response", PLOS Pathogens, vol. 10, No. 5, May 22, 2014, p. e1004152.

De La Fuente-Nunez C.et al., "Using anti-biofilm peptides to treat antibiotic-resistant bacterial infections", Postdoc Journal, vol. 3, No. 2, Feb. 1, 2015.

Jamali et al. "Prevalence, antimicrobial susceptibility and virulotyping of *Listeria* species and *Listeria monocytogenes* isolated from open-air fish markets", BMC Microbiology (2015) pp. 1-7.

Kundra et al., "Survival of the fittest: the relationship of (p)ppGpp with bacterial virulence", Frontiers in Microbiology, Dec. 2020, pp. 1-14.

Morales-Avila et al., "Antibacterial efficacy of gold and silver nanoparticles functionalized with ubiquicidin (28-41) antimicrobial peptide", Journal of Nanomaterials, Mar. 25, 2017, 10 pages.

Palmieri et al., "Bactericidal and antibiofilm activity of bactenecin-derivative peptides against the food pathogen Listeria monocytogens: New perspectives for food processing industry", International Journal of Food Microbiology, Available online Apr. 27, 2018, 33-42.

Palmieri G. et al., "New antimicrobial peptides against foodborne pathogens: fromin silicodesign to experimental evidence," Food Chemistry, vol. 211, May 17, 2016, pp. 546-554.

Reffuveille et al., "A broad-spectrum antibiofilm peptide enhances antibiotic action against bacterial biofilms", Antimicrobial Agents and Chemotherapy (2014) p. 5363-5371.

Search Report and Written Opinion of PCT/EP2018/069304 of Oct. 29, 2018.

* cited by examiner

*Primary Examiner* — Lianko G Garyu
(74) *Attorney, Agent, or Firm* — SILVIA SALVADORI, P.C.; Silvia Salvadori

(57) ABSTRACT

The present invention relates to the use of at least one peptide having sequence VRLIVAVRIWRR, VRLIVAVRIKRR, VRLIVKVRIWRR, VRLIVKVRIKRR (SEQ ID NO: 1, SEQ ID NO 2, SEQ ID NO 3, SEQ ID NO 4), as a bactericidal antimicrobial agent against *Listeria monocytogenes*.

12 Claims, 13 Drawing Sheets
Specification includes a Sequence Listing.

ANTIMICROBIAL PEPTIDES

This application is a continuation of U.S. patent application Ser. No. 16/630,615 filed Jan. 13, 2020, which is a U.S. National Stage of PCT/EP20181069304 filed 16 Jul. 2018, which claims priority to and the benefit of Italian Application No. 102017000080068 filed 14 Jul. 2017, the contents of which are incorporated herein by reference in their entireties.

Sequence listing SEQ.xml, created on Sep. 14, 2022 and of size of 5570 bytes is incorporated herein by reference.

FIELD OF THE INVENTION

The present invention relates to peptides having bactericidal activity towards *Listeria monocytogenes* and to their use as antimicrobial agents or in the treatment of listeriosis.

The invention also relates to products having the above peptides coated or immobilised on their surface.

BACKGROUND ART

The consumer's attention to the possible health effects related to food quality is having a major impact on the food processing and preservation industries. Compared to the past, today the consumer is increasingly aware and attentive to the quantity of chemical preservatives present in food and to the effectiveness of both conventional methods and innovative preservation technologies to extend durability and improve the safety of a wide range of food products. There are several microorganisms recognized today as responsible for food infections, i.e. related to the consumption of food, among these there is certainly *Listeria monocytogenes*, a Gram-positive bacterium, pathogen of Listerosis. In fact, this may contaminate a wide variety of foods, usually raw, such as not well cooked meat, raw vegetables, fish products, cheese prepared from unpasteurized milk or in ready-to-use food products that are industrially processed and require preservation at low temperatures. Once ingested, *Listeria monocytogenes* can cross intestinal, placental and cerebral barriers causing infections with different clinical features, inducing serious pathological events such as spontaneous abortions, meningoencephalitis, septicemia and gastroenteritis. Food-originated Listeriosis is a rather rare but serious disease, with a mortality rate of 20-0%, comparable to that of other food diseases such as salmonellosis. In relation to its incidence and severity, the economic and social impact of listeriosis is considered among the highest among foodborne diseases (Barbuddhe S B and Chakraborty T., 2009, Curr Top Microbiol Immunol 337:173-95; Barbuddhe S B et al., 2012, Int J Food Microbiol 154(3):113-8).

The contamination of food by this microorganism is very widespread and difficult to fight as it is able to adapt to different food storage and production processes conditions. In fact, *Listeria monocytogenes* can grow and reproduce at different pH conditions and at temperatures ranging from 0 to 45° C., thus persisting in the environment as well as in processed, stored and refrigerated foods. It has also been shown that *Listeria monocytogenes* is capable of resisting cleaning, sanitizing, drying and UV ray processes, thus increasing the likelihood of environmental contamination (Mullapudi S at al, 2008, Appl Environ Microbiol 74: 1464-8, Saá Ibusquiza P et al, 2011, Food Microbiol 28(3): 418-25) *Listeria monocytogenes* infections have traditionally been treated by administration of penicillins or carbapenems (Espaze E P and Reynaud A E, 1988, Infection 16 Suppl 2: S160-S164, Troxler R et al, 2000, Clin Microbiol Infect 6: 525-535). However, in recent years several *Listeria* strains have been identified, showing multiple resistance to antibiotics, including those of election for the treatment of the infection (Walsh D et al, 2001, J Appl Microbiol 90: 517-522, Prazac A M et al, J Food Prot. 65: 1796-1799, Charpentier E et al, 1995, J Infect Dis 172: 277-281). In particular, the most represented strain in clinical listeriosis isolates is the serotype 4b (Gilot P at al, 1996, J Clinical Microbiol 34(4): 1007-1010, Mammina C et al, 2009, J Clinical Microbiol 47(9): 2925-2930). This strain is more virulent than the reference ATCC (American Type Culture Collection) or NTCC (National Type Culture Collection) strain, available on the market. Moreover, the serotype 1/2c, which is one of the most frequently isolated from food, has revealed a specific resistance to penicillin G and ampicillin (Ayaz et al, 2010, J. Food protection 73: 967-972).

In view of the above, the need is felt to identify new molecules that allow an effective action of prevention and/or treatment of both contamination of products, in particular food, by *Listeria monocytogenes*, and listeriosis infections, in particular in the case of antibiotic-resistant strains.

In the last decade, the existence of natural peptides (called Antimicrobial Peptides or AMPs) having various and diverse antimicrobial activities has been recognized (De Smet K and Contreras R, 2005, Biotechnol Lett 18:1337-47). In humans and other mammals, these peptides have been identified as essential components of innate immunity, contributing to the first line of defense against infections (Henzler Wildman K A et al, 2003, Biochemistry 42(21): 6545-58; Bals R, 2000, Respir Res. 1(3):141-50, Agerberth B et al, 1999, Am J Respir Crit Care Med 160: 283-290).

The specific antimicrobial activity and the selectivity of AMPs depends on their chemical-physical properties such as: amphipathic characteristics, net charge, charge angle, total hydrophobicity and conformational flexibility (Teixeira V et al, 2012, Prog Lipid Res. 51(2):149-77, 2012, Palmieri G at al, 2016, Food Chem 211:546-54). In particular, the peptides show a structure-activity relationship for antibiofilm activity different from that requires for bactericidal activity against planktonic cells (De la Fuente-Núñez C, 2014, PLoS Pathog 10(5):e1004152).

In recent years, numerous peptides have been identified as potential new antimicrobial agents through various techniques such as screening and testing of natural host defence peptides, in silico analysis or screening of peptide libraries. Some of these peptides have shown an activity against bacterial biofilm formation, at concentrations often below their minimum inhibitory concentration (MIC) against the same bacterial cells in planktonic form. It has also been pointed out that the antimicrobial activity of the identified peptides does not appear in any way related to a bactericidal activity because the structure/function relationship of the peptides is different for the bactericidal or antibiofilm activities (Overhage J et al 2008, Infect Immun 76(9):4176-82, Amer L S et al, 2010, Biochem Biophys Res Commun 396(2):246-51, Pompilio et al, 2011, Peptides 32(9):1807-14, De la Fuente-Núñez C at al, 2012, Antimicrob Agents Chemother 56(5):2696-704, De la Fuente-Núñez C et al, 2014, PLoS Pathog 10(5):e1004152).

In particular, WO2015038339 describes 749 peptides having a sequence of 7-12 aminoacids, which are indicated as having a very specific antibiofilm and/or immunomodulatory activity. In this context, the peptide named IDR-1018, having sequence VRLIVAVRIWRR, (SEQ ID NO: 1), the peptide named IDR-1018-K6 or 2001, having sequence VRLIVKVRIWRR (SEQ ID NO: 3), and the peptide named IDR-1018-K10, having sequence VRLIVAVRIKRR (SEQ ID NO: 2) are disclosed. The antibiofilm activity of these peptides is demonstrated against a number of different microorganisms such as *Pseudomonas aeruginosa, Klebsiella pneumoniae, Staphylococcus aureus, E. coli*, and *Acinetobacter baumannii, Salmonella enterica* ssp. *Typhimurium* and *Burkholderia cenocepacia* or *Staphylococcus aureus* and *Pseudomonas aeruginosa*.

The antibiofilm activity of peptide 1018 against biofilms formed by *Pseudomonas aeruginosa, Klebsiella pneumoniae, Staphylococcus aureus, E. coli, Acinetobacter baumannii* and *Burkholderia cenocepacia* is also reported by the same authors in PLoS Pathog 10(5):e1004152.

The above documents disclose that the peptides show a specific antibiofilm activity that is independent of the bactericidal activity against cells in planktonic form and do not show any activity on planktonic cells at the concentrations tested.

In view of the above, in WO2015038339 it is suggested to combine the peptides with antibiotics that kill bacteria released from the biofilm once this is disrupted.

Bacteria belonging to the *Listeria* genus show very peculiar characteristics and there are numerous evidences demonstrating that peptides capable of an efficient growth inhibition of other bacteria show instead a scarce activity against *Listeria monocytogenes* (Gravesen A et al 2002, Microbiology 148:2361-2369, Gravesen A et al 2001, Microb Drug Resist 7:127-135, Rasch M and Knøchel S 1998, Lett Appl Microbiol 27:275-278).

Several studies have shown that, compared to other microorganisms such as *Pseudomonas* or *Staphylococcus*, the formation of biofilm is less critical in infections caused by *Listeria* since this pathogen has a lower capacity to form biofilms (Renier S et al, 2011, Environ Microbiol 13: 835-50, Djordjevic D et al, 2002, Appl Environ Microbiol 68:2950-2958, Borucki M K et al, 2003, Appl Environ Microbiol 69: 7336-7342, Harvey J at al, 2007, Food Microbiol 24: 380-92). More recently, assays carried out on a broad panel of *Listeria monocytogenes* strains isolated from clinical and food sources have shown an extreme variability and a poor tendency to the formation of biofilms (Doijad S P et al, 2015, PlosOne 10(9): 90137046, Borucki M K et al, 2003, Appl Environ Microbiol 69: 7336-7342). In particular, none of the strains from animal and human clinical cases showed a strong capacity of biofilm formation (Doijad S P at al, 2015, PlosOne 10(9):e0137046). In addition, the films formed by *Listeria* and the mechanisms by which the bacteria adhere to surfaces appear to be completely different from those of the other bacteria. In particular, *Listeria* does not secrete a sufficient amount of extracellular matrix polysaccharides to produce three-dimensional films as the bacteria listed above, but adhere to the surfaces through hydrophobic interactions forming bidimensional films (Silva E P et al, 2013 Appl Microbiol Biotechnol 97: 957-68, Doijad S P et al, 2015, PlosOne 10(9): 90137046).

In the case of *Listeria*, in order to effectively prevent or eliminate contamination by this microorganism, an antimicrobial agent having a strong bactericidal activity against planktonic cells is required. The actual treatment of *Listeria* contamination or infection with antibiotics finds a great limitation in the resistance developed by many strains of these bacteria. An ever-increasing number of *Listeria* strains appears to have a worrisome reduced susceptibility to various antibiotics such as ampicillins, penicillins and gentamicins (Facinelli B et al, 1991, Lancet 338: 1272, Safdar A and Armstrong D, 2003, J Clin Microbiol 41: 483-485, Popowska M et al, 2006, Pol J Microbiol 55: 279-288).

It is therefore strongly felt the need of identifying new antimicrobial agents against *Listeria* infections that show a strong bactericidal activity, optionally associated with an ability to also inhibit biofilm formation, especially against antibiotic resistant strains.

Molecules capable of performing both an effective bactericidal and antibiofilm activity against *Listeria* strains can significantly increase the levels of food safety, also ensuring better therapy and prophylaxis of listeriosis.

SUMMARY OF THE INVENTION

The present inventors have surprisingly found that the peptides IDR-1018 and IDR-1018-K6, the latter hereinafter referred to as Bac-amp1, and peptides exhibiting a sequence having the same features of length, basicity, net charge and hydrophobicity exhibit a bactericidal activity against *Listeria monocytogenes* with a MIC below 10 µM and a weak antibiofilm activity, with a MIC between 25 and 50 µM.

The biological activity observed for these peptides against *Listeria* is completely unexpected. In fact, this is significantly different from that disclosed by the prior art discussed above for the same peptides against other microorganisms, which showed an antibiofilm activity at low concentrations of peptide, at which no activity against planktonic cells was identified.

The aforesaid peptides represent excellent candidates able to meet the food safety requirements, reducing the levels of contamination upon consumption, and improving the prevention and prophylaxis from listeriosis, caused by the pathogenic agent *Listeria monocytogenes*.

Accordingly, a first object of the present invention is the use of at least one peptide, having sequence VRLIVAVRIWRR, VRLIVAVRIKRR, VRLIVKVRIWRR, VRLIVKVRIKRR (SEQ ID NO: 1, SEQ ID NO: 2, SEQ ID NO: 3, SEQ ID NO: 4), or a salt or solvate thereof, as an antimicrobial agent for the prevention and/or treatment (removal) of contamination of a product, preferably a food, a material, an object, or a surface by *Listeria monocytogenes*.

Furthermore, the present inventors have found that the peptides according to the invention show a high conformational stability even at extreme pH values (pH 1.0 or 11.0). In particular, the peptides of the invention such as for example Bac-amp1, show a greater conformational stability at pH 11.0; on the contrary, the peptides of the invention such as for example IDR-1018, have a higher conformational stability at pH 1.0. These properties make it possible to use these peptides, either individually or in combination, in acidic or basic environments, such as in the presence of chemical compounds used in sanitizing formulations. This allows the development of sanitizing eco-friendly bio-formulations with a lower concentration of chemical substances, acidic or strongly alkaline and, as a consequence, a reduced environmental impact.

Furthermore, an association of the two peptides indicated above is particularly advantageous, since it allows obtaining antimicrobial compositions effective within a very broad pH range.

Therefore, a second object of the invention is an antimicrobial composition comprising a mixture of at least one peptide having sequence VRLIVAVRIWRR, VRLIVAVRIKRR (SEQ ID NO: 1, SEQ ID NO: 2) and at least one peptide having sequence VRLIVKVRIWRR, VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

A third object of the invention is a peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4), or a pharmaceutically acceptable salt or solvate thereof, for use in the treatment of an infection from *Listeria monocytogenes* in a subject, preferably for use in the treatment of listeriosis.

A fourth object of the invention is a method for the treatment of an infection from *Listeria monocytogenes* in a subject, preferably listeriosis, by administering a peptide or a mixture of peptides having sequence VRLIVAVRIWRR, VRLIVAVRIKRR, VRLIVKVRIWRR, VRLIVKVRIKRR (SEQ ID NO: 1, SEQ ID NO: 2, SEQ ID NO: 3, SEQ ID NO: 4), or a pharmaceutically acceptable salt or solvate thereof.

A fifth object of the invention is a pharmaceutical formulation comprising at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4), or a pharmaceutically acceptable salt or solvate thereof.

According to a preferred embodiment, said at least one peptide is a mixture between at least one peptide having sequence VRLIVAVRIWRR, or VRLIVAVRIKRR (SEQ ID NO: 1, SEQ ID NO: 2) and at least one peptide having sequence VRLIVKVRIWRR, or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

A sixth object of the invention is a coating composition comprising at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4).

A seventh object of the present invention is a product having at least one surface covered with a coating adherent to said surface comprising at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4).

The present inventors have also surprisingly found that when the N-terminal amino group of the above peptides are linked covalently to the surface of a product, the bactericidal activity of the free peptides is maintained.

Accordingly, an eighth object of the invention is a product having at least one surface, covalently linked to at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4).

A ninth object of the invention is a liquid antimicrobial composition comprising the nanoparticles comprising, covalently linked to their surface, at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4).

A tenth object of the invention is the use of nanoparticles comprising, covalently linked to their surface, at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4) as an antimicrobial agent for the prevention or treatment of contamination of a product or surface by bacteria.

An eleventh object of the invention is a method for the treatment of a bacterial infection in a subject, by administering nanoparticles comprising, covalently linked to their surface, at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4).

A twelfth object of the invention is a pharmaceutical composition comprising nanoparticles comprising, covalently linked to their surface, at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4), optionally in combination with pharmaceutically acceptable excepients or carriers.

FIGURES

FIG. 1 and FIG. 2 show the Circular Dichroism (CD) spectra of the Bac-amp1 and IDR1018 peptide, respectively, obtained in the presence of 10 mM SDS under different temperature conditions, as described in Example 2a FIG. 3 and FIG. 4 show the Circular Dichroism (CD) spectra of the Bac-amp1 and IDR1018 peptide, respectively, obtained in the presence or absence (SDS) of 10 mM SDS at different pH conditions, as described in Example 2b. The diagrams show in particular the average molar ellipticity values per residue×$10^{-3}$, expressed in degrees $cm^2/dmol$, as the wavelength varies.

The folding kinetics of the Bac-amp1 peptide was monitored for 24 h at 25° C. by CD spectroscopy (C) and fluorescence (D) techniques after the addition of SDS at a final 10 mM concentration.

FIG. 5 shows a chromatogram obtained by RP-HPLC chromatography performed on samples of the IDR-1018 or Bac-amp1 peptide incubated in mozzarella brine for 24 h at 4° C. as described in Example 2c. The diagram shows the absorbance values at 220 nm as a function of the volume of eluate, measured in ml.

FIG. 6 shows the dose-response curve obtained with the Bac-amp-1 peptides against *S. aureus, S. typhimurium, L. monocytogenes, L. monocytogenes* and *L. monocytogenes*, expressed as % of colony forming units (CFU) observed on plates seeded with the bacterial cultures upon incubation in the presence of different peptide concentrations, as described in Example 3, with respect to the corresponding control plates without peptide.

FIG. 7 and FIG. 8 show the box-plot graphs, which are a graphical representation used to describe the distribution of a sample by means of simple dispersion and position indices, obtained by using the Graphpad Prism software. The figures show the absorbance values at 492 nm measured after staining with crystal violet of steel discs incubated with a standardized inoculum of *L. monocytogenes* for 72 h and at 37° C. in absence (Ctrl) or in the presence of different concentrations of Bac-amp1 or IDR-1018 peptide, respectively, as described in Example 4a.

FIG. 9 shows the images at different magnifications obtained with the scanning electron microscope (SEM) of steel discs treated with a standardized inoculum of *L. monocytogenes* in the presence of the Bac-amp1 peptide (FIG. 9a, magnification ×1000; FIG. 9c, magnification ×5000) at the concentration 50 µM, or only with control medium (FIG. 9b, magnification ×1000; FIG. 9d, magnification ×5000), as described in Example 4b.

FIG. 10 shows the images at different SEM magnifications of steel discs treated with standardized inoculum of *L.* monocytogenes in the presence of the IDR-1018 peptide (FIG. 10a, magnification ×1000; FIG. 10b, magnification ×5000) at the concentration 50 µM, as described in Example 4b.

Figure 13:
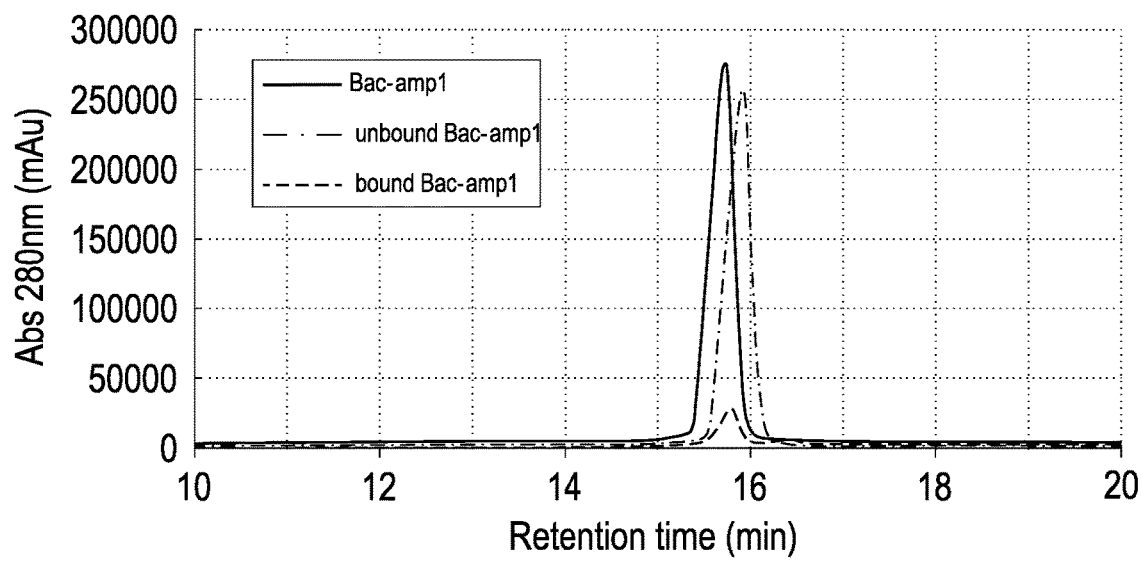

FIG. 13 shows HPLC quantification of the peptide grafted to gold nanoparticles, as described in Example 8. Specifically the chromatograms show the absorbances obtained with a reference solution with initial (at time=0) peptide concentration (Bac-amp1), the supernatant solution at the end of the functionalization reaction (unbound Bac-amp1), and the supernatant solution after cleavage of the peptide from the surface of the nanoparticles (bound Bac-amp1).

Figure 14:
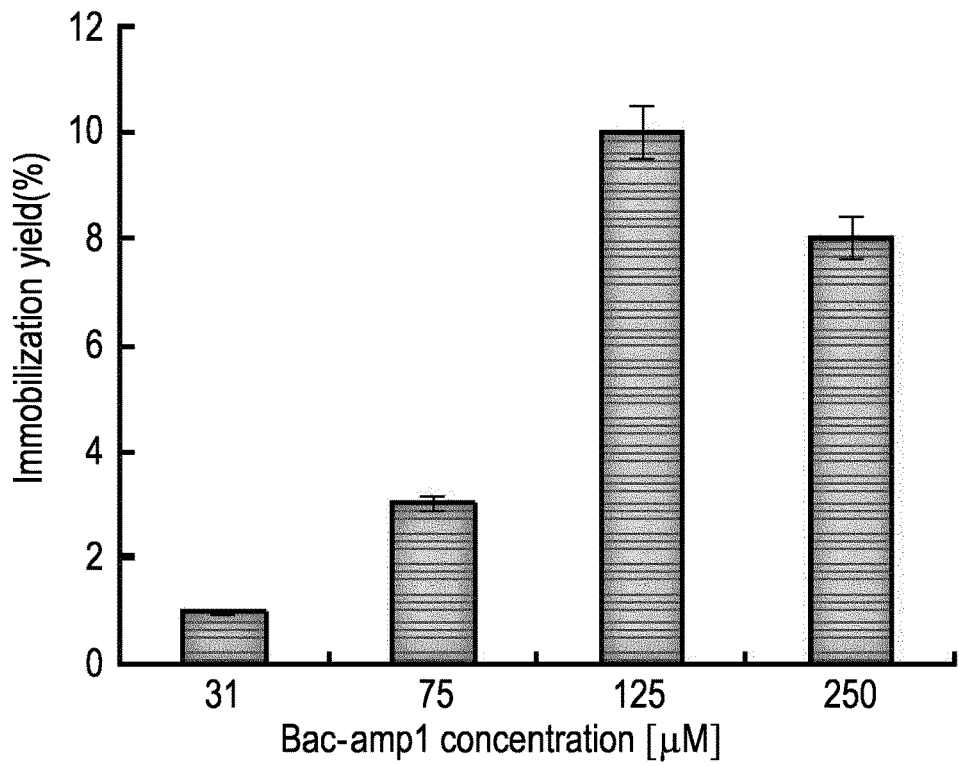

FIG. 14 shows the titration curve for gold nanoparticles functionalization with Bac-amp1 peptide as function of peptide concentration. Immobilization yields obtained with Bac-amp1 concentrations of 31, 75, 125 or 250 µM are shown.

Figure 15:
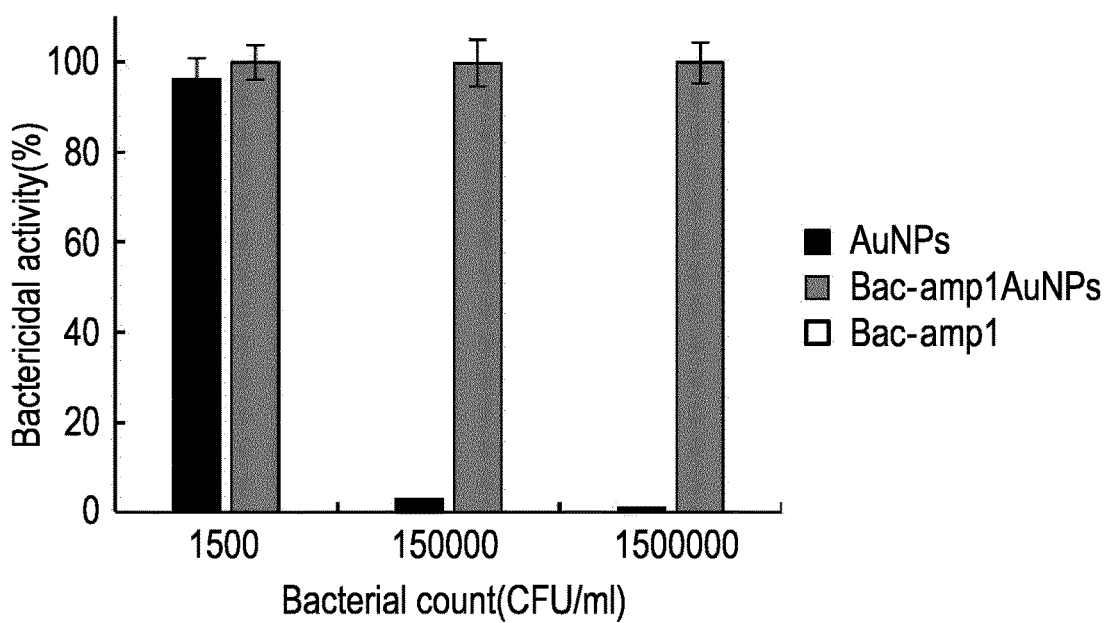

FIG. 15 shows the bactericidal activity against *Listeria monocytogenes* cells at the indicated concentrations (CFU/ml), expressed as percentage of bacterial cells killed, of gold nanoparticles either covalently linked to peptide Bac-amp1 (Au-NPs-Bac-amp1, grey bar) or without the peptide (Au-NPs, black bar), at a concentration of 0.16 µM).

Figure 16:
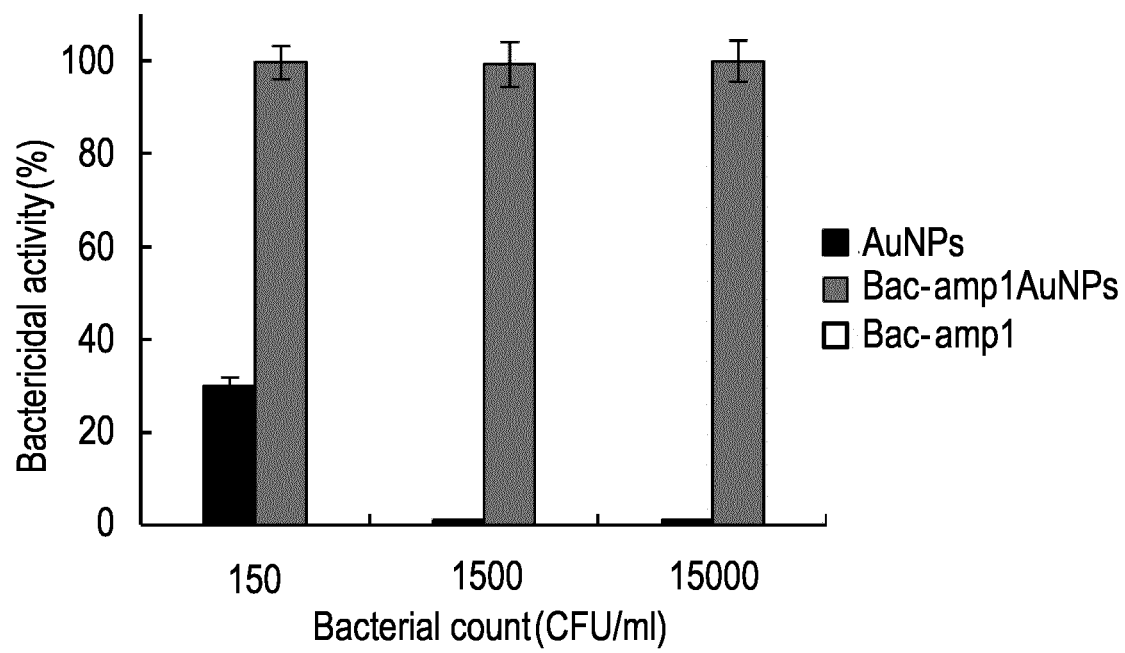

FIG. 16 shows the bactericidal activity against *S. Typhimurium* cells at the indicated concentrations (CFU/ml), expressed as percentage of bacterial cells killed, of the peptide Bac-amp1 covalently linked (concentration of 0.16 µM) to the gold nanoparticles (Au-NPs-Bac-amp1, grey bar) or gold nanoparticles without the peptide (Au-NPs, black bar).

Figure 17:
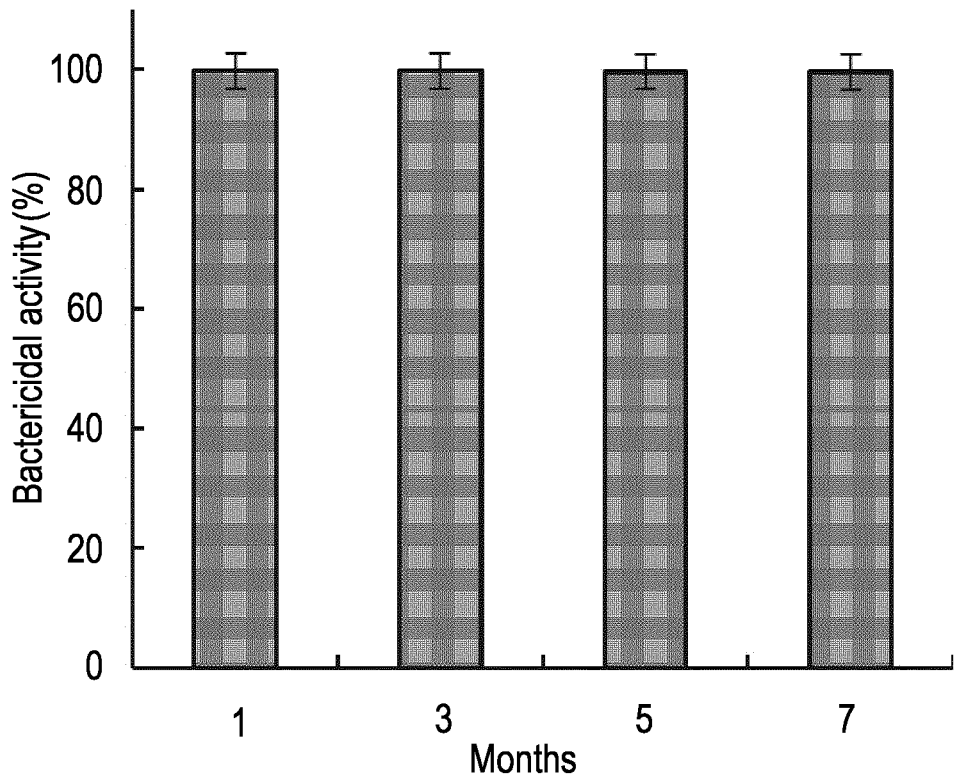

FIG. 17 shows the long-term stability of bactericidal activity against *Listeria monocytogenes* for a period of up to 7 months.

Figure 18:
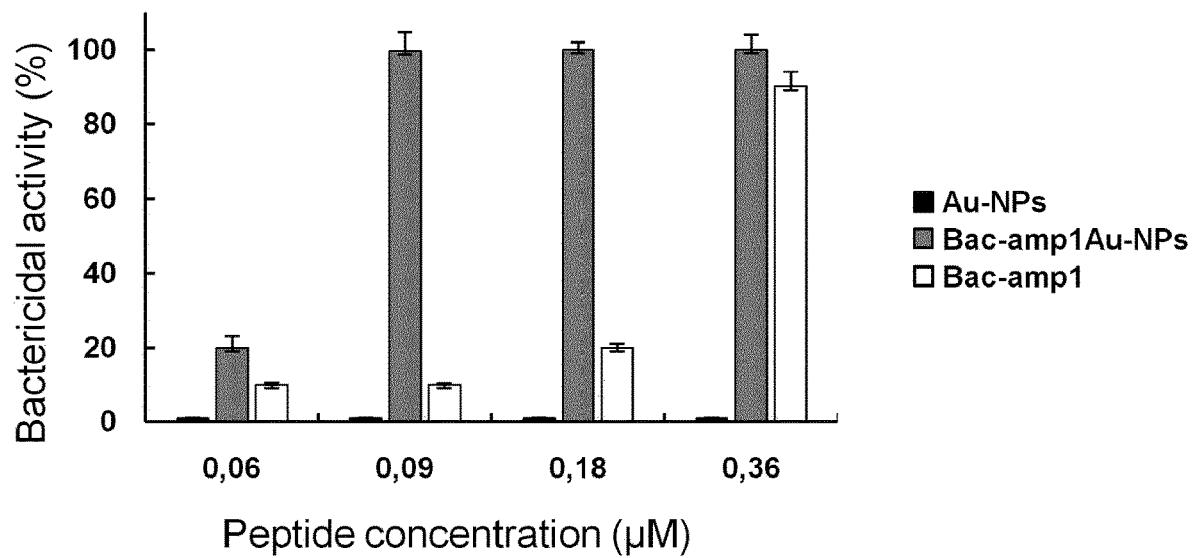

FIG. 18 shows the bactericidal activity of the peptide free (at a concentration of 0.16 µM) or covalently linked (at a concentration of 0.16 µM) to nanoparticles against *Listeria monocytogenes* at the indicated concentrations (CFU/ml).

DEFINITIONS

The term "biofilm" according to the present invention refers to bacterial cells embedded within an extracellular matrix composed of extracellular polymeric substances and attached to a living or abiotic surface.

The expressions "antibiofilm" or "biofilm inhibition activity" according to the present invention refers to the ability of peptides to prevent or inhibit the formation of biofilm of bacteria or to inhibit the growth of bacteria in biofilm.

The expression "bactericidal activity" according to the present invention means the ability of peptides to kill planktonic (free swimming) bacterial cells (bactericidal activity against the planktonic cells).

Potency of antibiofilm or bactericidal activity, as defined above, of a peptide compound (a protein chain consisting of at least 10 amino acids) against a specific microorganism is considered in the art to be suitable for an use as antimicrobial or therapeutic agent when the minimum inhibitory concentration (MIC) and/or the minimum biofilm inhibitory concentration (MBIC) of that compound against that microorganism is no more of 20 µM.

Active concentrations (MIC; MBIC) for such peptides higher than 20 µM would result in uncompetitive costs for applications in different industrial fields.

The expression "antimicrobial activity" according to the present invention means the ability to prevent or eradicate a bacterial infection in a living organism or on a product, such as a food, a material or an object.

The expressions "antimicrobial agent" or "antimicrobial composition" according to the present invention refers to a compound or a composition, respectively, having an antimicrobial activity.

The expression "solvates" according to the present invention means complexes of the peptides of the invention with the solvents in which the synthesis reaction takes place or in which they are precipitated or crystallized. For example, a complex with water is known as a "hydrate".

The expression "hybrid nanoparticle" according to the present invention refers to a nanoparticle composed of inorganic compounds, preferably one or more metals, more preferably silver or gold and organic compounds, preferably one or more polymers, more preferably polyethylene glycol (PEG) made from polymerized ethylene glycol (ethane-1,2-diol) units. The hybrid nanoparticles according to the invention comprise a polymer component with different functional end reactive groups, such as PEG diamine and PEG-mercaptoethyl ether acetic or PEG diacid.

DETAILED DESCRIPTION OF THE INVENTION

As will be shown in the experimental section, the present inventors have identified that the peptides IDR-1018, having sequence VRLIVAVRIWRR (SEQ ID NO: 1) and Bac-amp1, having sequence VRLIVKVRIWRR (SEQ ID NO: 3) are endowed with a potent bactericidal activity showing MIC concentrations in the low micromolar range against *Listeria monocytogenes*. This is unexpected in view of the activity of these peptides against other microorganisms disclosed in the prior art, which showed a selective antibiofilm activity and no bactericidal activity at the concentrations tested. Therefore, a first object of the invention is the use of at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4), or a salt or solvate thereof, as an antimicrobial agent for the prevention and/or treatment (removal) of contamination of a product or a surface by *Listeria monocytogenes*.

The above product may be any product susceptible of contamination by *Listeria*, such as for example a food product, a material or an object.

Preferably, said product is an object, such as a container or a tool or operating part of a machine, or a material, such as a packaging material, preferably for the storage or processing of food.

Preferably, said surface is a surface a facility for the processing or storage of food.

Preferably, the use according to the first object of the invention is for the sanitization of facilities or machinery intended for processing food products.

Said antimicrobial agent has a bactericidal activity against *Listeria* planktonic cells with a MIC at concentrations below 10 µM, preferably below 5 µM, more preferably below 1 µM.

Depending on the peptide and on the strain of *Listeria* involved in the infection, the antimicrobial agent may also have an antibiofilm activity.

Preferably, said antimicrobial agent has a combined bactericidal activity and antibiofilm activity against *Listeria*.

Preferably, said at least one peptide is used at concentrations of up to 10 µM, more preferably, below 8 µM, more preferably below 5 µM, even more preferably below 3 µM.

Preferably, said at least one peptide is used at concentrations between 0.5 and 10 µM, more preferably between 0.5 and 8 µM, more preferably between 0.5 and 5 µM, even more preferably between 0.5 and 3 µM.

Particularly preferred is the use of the peptides according to the invention VRLIVAVRIWRR or VRLIVKVRIWRR (SEQ ID NO:1, SEQ ID NO: 3), more preferably, the use of a peptide VRLIVKVRIWRR, (SEQ ID NO: 3).

Salts or solvates suitable for the purposes of the invention are those which do not lead to a conformational or stability modification of the peptides according to the invention and, therefore, do not interfere with their biological activity.

As will be shown in the experimental section, the peptides of the invention exhibit a strong bactericidal activity. The high bactericidal activity of the peptides against *Listeria monocytogenes* allows obtaining an effective prevention or eradication of this microorganism without necessarily having to associate it with other bactericidal compounds such as, for example, antibiotics.

Therefore, according to a preferred embodiment of the invention, said at least one peptide is not in association with bactericidal compounds, preferably it is not in association with an antibiotic.

As shown in the experimental section, the peptides of the invention exhibit a high bactericidal activity against *Listeria monocytogenes* and, in particular, also against strains of this bacterium isolated from contaminated food and environmental samples and belonging to serotype 4b or to serotype 1/2c, which are more virulent than the reference ATCC (American Type Culture Collection) or NTCC (National Type Culture Collection) strains commercially available, and are resistant to various antibiotics (Ayaz et al, 2010, J. Food protection 73: 967-972).

Therefore, preferably said *Listeria monocytogenes* is an antibiotic-resistant *Listeria monocytogenes* serotype, more preferably it is a *Listeria monocytogenes* serotype resistant to one or more antibiotics selected from cephalosporins, ampicillins, tetracyclines, erythromycins and penicillins. Preferably, said serotype is a serotype 4b or 12c.

Surprisingly, the peptide having sequence VRLIVKVRIWRR (SEQ ID NO:3) shows a significantly more potent bactericidal activity against field strains of this bacterium, in particular strains belonging to serotype 4b or to serotype 1/2c, compared to that observed against the reference ATCC strain.

More preferably, said *Listeria monocytogenes* serotype is an antibiotic-resistant *Listeria monocytogenes* serotype, more preferably a *Listeria monocytogenes* serotype resistant to one or more antibiotics selected from cephalosporins, ampicillins, tetracyclines, erythromycins and penicillins, even more preferably a serotype 4b or 1/2c and said at least one peptide is VRLIVKVRIWRR (SEQ ID NO:3).

According to a further preferred embodiment, the use according to the first object of the invention is as a preservative agent of food products, in particular for the prevention and/or treatment of contamination thereof by *Listeria monocytogenes*.

Preferably, according to this embodiment, said use provides applying at least one peptide according to the invention on the surface and/or inside the body of the food product. Alternatively, said use provides applying at least one peptide according to the invention on the surface of food packaging.

As will be shown in the experimental section, the two peptides have a high stability to temperature and pH variations and are therefore particularly suitable to be used in the functionalization of materials used for food packaging, maintaining their activity also following the production steps of the materials themselves.

In particular, the present inventors have found that the peptides according to the invention show a high conformational stability even at extreme pH values (pH 1.0 or 11.0). In particular, the peptides of the invention VRLIVKVRIWRR or VRLIVKVRIKRR (SEQ ID NO: 3, SEQ ID NO: 4), such as Bac-amp1, show a greater conformational stability at pH 11.0; on the contrary, the peptides of the invention VRLIVAVRIWRR or VRLIVAVRIKRR (SEQ ID NO: 1, SEQ ID NO: 2), such as for example IDR-1018, show a greater conformational stability at pH 1.0.

Accordingly to the first object of the invention the peptide having sequence VRLIVAVRIWRR (SEQ ID NO:1) is used for the packaging of food products with a pH value in the range 1.0-4.0 preferably 4.0, while the peptide having a sequence VRLIVKVRIWRR (SEQ ID NO:3) is used for the packaging of food products having a pH up to 11, preferably of 8.0. More preferably, the use accordingly to the first object of the invention provides that in food packaging, a mixture is used of at least one peptide having a sequence VRLIVAVRIWRR or VRLIVAVRIKRR (SEQ ID NO: 1, SEQ ID NO: 2) and at least one peptide having sequence VRLIVKVRIWRR or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

An association between the aforesaid peptides is particularly advantageous as it allows having an antimicrobial composition, which is effective and resistant in a very wide pH range.

Preferably, in the use according to the first object of the invention, said at least one peptide is a mixture between at least one peptide having sequence VRLIVAVRIWRR or VRLIVAVRIKRR (SEQ ID NO: 1, SEQ ID NO: 2) and at least one peptide having sequence VRLIVKVRIWRR or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

Furthermore, in accordance with the above, a second object of the invention is an antimicrobial composition comprising a mixture of at least one peptide having sequence VRLIVAVRIWRR or VRLIVAVRIKRR (SEQ ID NO: 1, SEQ ID NO: 2) and at least one peptide having sequence VRLIVKVRIWRR or VRLIVKVRIKRR (SEQ ID NO: 3, SEQ ID NO: 4), preferably comprising a mixture between the peptide having sequence VRLIVAVRIWRR (SEQ ID NO: 1) and the peptide having sequence VRLIVKVRIWRR (SEQ ID NO: 3).

The peptide or mixture of peptides according to the invention is also useful in the treatment of diseases caused by *Listeria monocytogenes*, in particular in the treatment of listeriosis.

Therefore, a third object of the invention is a peptide or a mixture of peptides having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4), or a pharmaceutically acceptable salt or solvate thereof, for use in the treatment of an infection from *Listeria monocytogenes* in a subject, preferably for use in the treatment of listeriosis.

A fourth object of the invention is a method for the treatment of an infection from *Listeria monocytogenes* in a subject, preferably listeriosis, by administering a peptide or a mixture of peptides having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4), or a pharmaceutically acceptable salt or solvate thereof.

Preferably, according to the third or fourth object of the invention, said subject is a mammal, more preferably it is a human.

According to a preferred embodiment of the third or fourth object of the invention, said peptide or mixture of peptide is or comprises a peptide VRLIVKVRIWRR (SEQ ID NO:3).

Salts or solvates according to the third or fourth object of the invention are pharmaceutically acceptable salts which do not lead to a conformational or stability modification of the peptides according to the invention.

Pharmaceutically acceptable acid addition salts include those formed with hydrochloric, hydrobromic, acetic, phosphoric, lactic, pyruvic, acetic, trifluoroacetic, succinic, perchloric, fumaric, maleic, glycolic, lactic, salicylic, oxaloacetic, methanesufonic, ethanesulfonic, p-toluenesulfonic, formic, benzoic, malonic, naphthalene-2-sulphonic, benzenesulfonic and isetionic acids. Other acids, such as oxalic acid, although not per se pharmaceutically acceptable, may be useful as intermediates for obtaining the compounds of the invention and their pharmaceutically acceptable salts. Base salts, considered acceptable, include ammonium salts, alkali metal salts, for example potassium and sodium salts, alkaline earth metal salts, for example calcium and magnesium salts and salts with organic bases, for example dicyclohexylamine and N-methyl-D-glucosamine.

According to a preferred embodiment of the third or fourth object of the invention, said mixture of peptides is a mixture between at least one peptide having sequence VRLIVAVRIWRR, or VRLIVAVRIKRR (SEQ ID NO: 1, SEQ ID NO: 2) and at least one peptide having sequence VRLIVKVRIWRR, or VRLIVKVRIKRR (SEQ ID NO: 3, SEQ ID NO: 4), preferably it is a mixture between the peptide having sequence VRLIVAVRIWRR (SEQ ID NO: 1) and the peptide having sequence VRLIVKVRIWRR (SEQ ID NO: 3).

In the case of oral administration, the association of the aforesaid peptides allows overcoming the technical problem related to the decrease in the amount of peptide absorbed following the degradation of the peptides to the acidic or basic pH encountered at the level of the gastrointestinal system. The compatibility of the two peptides at the two opposite ends of pH causes a greater amount of active peptide to be absorbed and reach the site of action.

Preferably, said listeriosis is caused by an antibiotic-resistant *Listeria monocytogenes* serotype, more preferably a serotype resistant to one or more antibiotics selected from cephalosporins, ampicillins, tetracyclines, erythromycin and penicillins. More preferably, said Listeriosis is caused by a strain belonging to serotype 4b or 1/2c.

More preferably, said *Listeria monocytogenes* serotype is an antibiotic-resistant *Listeria monocytogenes* serotype, more preferably a *Listeria monocytogenes* serotype resistant to one or more antibiotics selected from cephalosporins, ampicillins, tetracyclines, erythromycins and penicillins, even more preferably a serotype 4b or 1/2c and said peptide is or said mixture of peptides comprises VRLIVKVRIWRR (SEQ ID NO:3).

A fifth object of the invention is a pharmaceutical formulation or composition comprising at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4), or a pharmaceutically acceptable salt or solvate thereof, optionally in combination with pharmaceutically acceptable excipients or carriers.

According to a preferred embodiment of the fifth object of the invention, said at least one peptide is a mixture between at least one peptide having sequence VRLIVAVRIWRR or VRLIVAVRIKRR (SEQ ID NO: 1, SEQ ID NO: 2) and at least one peptide having sequence VRLIVKVRIWRR or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

The pharmaceutical formulations according to the invention comprise those suitable for oral, parenteral (including subcutaneous, intradermal, intramuscular, intravenous and intra-articular) use, by inhalation (including powders of particularly small particles or mists which can be generated by means of various types of pressurized aerosol dispensers, nebulizers or insufflators), although the most suitable route may depend, for example, on the recipient's condition.

The formulations can conveniently be presented in unit dosage form and can be prepared by any of the well-known protocols of pharmaceutical technique. All the methods provide for the step of associating the active ingredient with the carrier, which constitutes one or more a pharmaceutically acceptable accessory ingredients. In general, the formulations are prepared in a uniform manner by associating the active ingredient with finely divided solid or liquid supports or both and then, if necessary, by formulating the product in the desired formulation.

The formulations of the present invention suitable for oral administration can be presented in discrete units such as capsules, cachets or tablets, each containing a predetermined amount of the active ingredient; such as powder or granules; as a solution or suspension in an aqueous liquid or a non-aqueous liquid; or as a liquid oil-in-water emulsion or as a liquid water-in-oil emulsion. The active ingredient may also be presented as bolus, electuary or paste. Several pharmaceutically acceptable carriers are described in standard formulation works, for example Remington's Pharmaceutical Sciences by E. W. Martin. See also Wang, Y. J. and Hanson, M. A., Journal of Parenteral Science and Technology, technical report no. 10, Supp. Compositions for oral administration include suspensions which may contain, for example, microcrystalline cellulose for imparting mass, alginic acid or sodium alginate as suspending agent, methylcellulose as a viscosity enhancer and sweeteners or flavouring agents such as those already known in the pharmaceutical industry; immediate release tablets which may contain, for example, microcrystalline cellulose, calcium phosphate, starch, magnesium stearate and/or lactose and/or other excipients, binders, extenders, disintegrants, diluents and lubricants such as those known in pharmaceutical techniques Parenteral administration formulations include solutions for aqueous and non-aqueous sterile injection that may contain antioxidants, buffers, bacteriostatic compounds, and solutes that make the formulation isotonic; aqueous and non-aqueous sterile suspensions, which may include surfactants and thickeners. The formulations may be presented in unit dose containers or in multi-dose containers, such as vials and sealed vials, and may be stored in a lyophilized form requiring only the addition of the sterile liquid support immediately prior to use. Compositions for administration of inhalation or nasal aerosols include salt solutions which may contain, for example, benzyl alcohol or other appropriate preservatives, which promote absorption to improve bioavailability and/or other solubilizing agents such as those known in the pharmaceutical technique. In compositions for administration of inhalation or nasal aerosols, the compound of the invention is administered in the form of an aerosol from a pressurized container or a nebulizer, using a suitable propellant, for example dichlorodifluoromethane, trichlorofluoromethane, dichlorotetrafluoroethane, carbon dioxide or other suitable gas. In the case of a pressurized aerosol, the dose unit can be determined by providing a valve to provide a measured amount. The preferred unit dosage formulations are those containing an effective dose, as described above, or an appropriate fraction, of the active ingredient.

It should be noted that, in addition to the ingredients specifically mentioned above, the formulations of the present invention may include other conventional agents in use in pharmaceutical techniques taking into account the type of formulation in question, for example those suitable for oral administration may include flavouring agents. The compounds of the invention are also appropriately administered as continuous and controlled release systems. Suitable examples of continuous release systems of the invention include suitable polymeric materials, such as semi-permeable polymeric matrices, such as films or microcapsules; specific hydrophobic materials, such as emulsions in suitable oils or ion exchange resins; and derivatives of the compound of the invention, such as, for example, a soluble salt.

According to embodiments of the use according to the first object of the invention, also in combination with other preferred embodiments described above, the at least one peptide may be applied to the surface of the product or surface to be protected or treated from contamination by *Listeria* by means of incorporation in a coating applied on said surface by covalent bonding to reactive groups present on said surface.

This allows to prolong the period of permanence of bactericidal concentrations of the peptide on the surface to be protected from contamination and thus to exert along lasting protective activity on said surface.

According to one embodiment of the use according to the first object of the invention, said at least one peptide is applied as a coating composition on the surface of said product or on said surface.

In this case, the use of the peptide or mixture of peptides according of the first object of the invention provides applying a liquid antimicrobial composition comprising said at least one peptide and, optionally, film forming polymers, to the surface of said product and then drying, thereby forming a coating.

A sixth object of the invention is therefore a coating composition comprising at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4).

Said coating composition preferably further comprises film-forming agents. These are compounds that are able to form a film on the surface of said object or material, which favours the permanence of the peptide or mixture of peptides thereon. Preferably, said film forming agent is a film-forming polymer.

A seventh object of the present invention is a product having at least one surface covered with a coating adherent to said surface, said coating comprising at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4) and, optionally, a film forming polymer.

Said coating may cover a part or the whole of the said surface.

Preferably, said product is a material or an object, as above defined.

According to a preferred embodiment of the sixth or seventh object of the invention, said at least one peptide is a mixture between at least one peptide having sequence VRLIVAVRIWRR, or VRLIVAVRIKRR (SEQ ID NO: 1, SEQ ID NO: 2) and at least one peptide having sequence VRLIVKVRIWRR, or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

According to another embodiment of the use according to the first object of the invention, said at least one peptide is linked with a covalent bond to the surface of said product or on said surface.

In fact, as will be shown in the Examples, the present inventors have found that when the N-terminal group of the above peptide is linked covalently to a surface, the bactericidal activity is maintained notwithstanding the conformational constrains of the linked peptide.

In this case, the use of the peptide or mixture of peptides provides that the peptide or mixture of peptides according to the invention is applied by forming a covalent bond with reactive groups present on a surface. This allows obtaining a product with a surface characterized by a bactericidal activity against *Listeria monocytogenes*, which is stable for long periods of time.

According to another embodiment of the use according to the first, third of fourth object of the invention, said at least one peptide may be linked with a covalent bond to the surface of nanoparticles that can be used as antimicrobial agents.

Accordingly, an eighth object of the invention is a product having at least one surface covalently linked to at least one peptide having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: and SEQ ID NO: 4).

Preferably, said peptide is linked to said surface by means of a covalent bond between the N-terminal amino group of the peptide and a chemical group on said surface.

Said peptide may be linked to a part or the whole of the said surface. Preferably, according to the eight object of the invention, said at least one peptide is a mixture between at least one peptide having sequence VRLIVAVRIWRR, or VRLIVAVRIKRR (SEQ ID NO: 1, SEQ ID NO: 2) and at least one peptide having sequence VRLIVKVRIWRR, or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3). Said product may be any product having a surface bearing chemical groups able to form a covalent bond with the N-terminal amino group of the peptide. Preferably said chemical groups are selected from a carboxyl groups, excited hydroxyl radicals, activated alkoxy groups or activated aldehyde or ketone groups.

Preferably, said product having at least one surface is an object, such as for example a container for storing food, a tool or operating part of a machine, for example used in food processing or a material, such as for example a packaging material, a polymer, a metal or a semiconductor.

Techniques for binding amino groups of peptides or proteins to surfaces are known to those skilled in the art and vary according to the material used.

For example, in the case of materials having surfaces in metal (gold, platinum silver) and semiconductors (titanium, zinc, tin, zirconium, and germanium), a silanization process may be used. This involves, for example, the reaction with the material to be treated of a mixture of sulfuric acid ($H_2SO_4$) and oxygen peroxide ($H_2O_2$), which are capable of activating the aforementioned surfaces by creating bonds of surface atoms and hydroxyl groups (—OH) easily replaceable by more stable bonds such as Si—C or Au—S. The activated surfaces can covalently bind the peptides of interest following treatment with a silanizing agent, such as aminopropyldimethylethoxysilane or aminopropyltritoxysilane, and a compound having two functional groups capable of forming the peptide covalent bond with the peptide amino groups, such as gluteraldehyde or bis-succinimide. These treatments are typical of the chemistry of aqueous solutions and for this reason they are called wet processes, which are advantageous because they do not require particular technological equipment but are limited to preferably rigid materials that can be wetted and dried without difficulty.

In the case of plastic or polymeric surfaces, these can instead be functionalized to hook the peptides of interest either by applying the wet processes described above, or by applying hi electromagnetic energy radiation (for example by laser, ultraviolet radiation, gamma rays). For so-called soft materials such as non-rigid plastics, wet processes may not be completely effective, so the so-called dry functionalization processes based on the interaction of the surface with a gaseous plasma or an electromagnetic radiation are preferred. The interaction of the surface of a polymer with electromagnetic radiation causes surface activation through the breaking of accessible polymeric bonds, so the C═C bonds become —C—C— allowing the subsequent chemical modification of the surface itself. The same operating principle applies to the other method of activation of the polymer surfaces and consists in the treatment thereof with ionized gas (gaseous plasma). This process is particularly advantageous because, since plasma is cold, the temperature of the treated material does not reach high values with respect to the ambient temperature. This method requires low pressure (0.1-100 Pa) and the presence of a working gas (usually N2, O2 or Ar, CF4) [Hegemann, Dirk, Herwig Brunner, and Christian Oehr. "Plasma treatment of polymers for surface and adhesion improvement" Nuclear instruments and methods in physics research section B: Beam interactions with materials and atoms 208 (2003): 281-286].

According to a particularly preferred embodiment of the eighth object of the invention, said product consists in nanoparticles. As will be shown in the experimental section, when the peptide of the invention is linked on the surface of nanoparticles, the bactericidal activity is surprisingly significantly increased. Furthermore, the peptide shows stability over a long period of time.

Accordingly, a particularly preferred object of the invention are nanoparticles comprising, covalently linked to their surface, at least one peptide according to the invention as described above, having sequence VRLIVAVRIWRR, or VRLIVAVRIKRR, or VRLIVKVRIWRR, or VRLIVKVRIKRR (SEQ ID NO: 1, SEQ ID NO: 2, SEQ ID NO: 3, SEQ ID NO: 4).

Preferably, said at least one peptide is a mixture of at least one peptide having sequence VRLIVAVRIWRR, or VRLIVAVRIKRR (SEQ ID NO: 1, SEQ ID NO: 2) and at least one peptide having sequence VRLIVKVRIWRR, or VRLIVKVRIKRR (SEQ ID NO: 3, SEQ ID NO: 4), preferably a mixture between the peptide having sequence VRLIVAVRIWRR (SEQ ID NO: 1) and the peptide having sequence VRLIVKVRIWRR (SEQ ID NO: 3).

Preferably, said peptide is linked to said surface of the nanoparticles by means of a covalent bond between the N-terminal amino group of the peptide and a chemical group on said surface.

Preferably, the N-terminal amino group of said at least one peptide is covalently bound to a chemical group on the surface of said nanoparticles selected from carboxyl groups, excited hydroxyl radicals, hydroxyl radicals, activated alkoxy groups or activated aldehyde or ketone groups.

Preferably, said at least one peptide is linked substantially uniformly over the whole surface of the nanoparticles.

Preferably, said nanoparticles have an average hydrodynamic diameter measured by dynamic light scattering (DLS) comprised between 5 and 90 nm, preferably between 5 and 70 nm, preferably between 5 and 50 nm, preferably between 5 and 40 nm, preferably between 5 and 30 nm, preferably between 5 and 30 nm, or more preferably of 15 nm.

Preferably, said nanoparticles are hybrid nanoparticles, more preferably are hybrid metal nanoparticles, even more preferably silver or gold hybrid nanoparticles.

Preferably, said hybrid nanoparticles contain a polymer as organic component, preferably selected from PEG molecules functionalized with different reactive groups, such as PEG diamine and PEG-mercaptoethyl ether acetic and PEG diacid.

The above nanoparticles may be used to deliver the peptides according to the invention to their site of activity.

Accordingly, in a preferred embodiment of the first, third or fourth object of the invention said at least one peptide is linked to the surface of nanoparticles according to the invention as above described.

Nanoparticles particularly suitable for therapeutic delivery of active compounds are natural materials or derivatives (chitosan, dextrane, gelatine, liposomes, alginates, starch), dendrimers, fullerenes, polymer carriers (polylactic acid, poly(cyano) acrylates, polyethileinemine, polycaprolactone), metallic nanoparticles, quantum dots, silica nanoparticles.

Accordingly, in the above embodiment of the tenth, eleventh or twelfth object of the invention, the nanoparticles are made of a material or a combination of material selected from the above.

As will be shown in the experimental section, the present inventors have surprisingly found that the nanoparticles according to the invention are able to increase the bactericidal activity of the peptides not only against *Listeria* but also against bacteria different from *Listeria monocytogenes*.

Therefore, the above described nanoparticles may be advantageously used to prevent or treat contamination or infections by many other bacteria.

The above nanoparticles according to the invention can be dispersed in a liquid composition that can be used as an antimicrobial composition.

Accordingly, a ninth object of the invention is a liquid antimicrobial composition comprising the nanoparticles according to the invention, as described above.

A tenth object of the invention is the use of the above nanoparticles according to the invention as an antimicrobial agent for the prevention or treatment of contamination of a product or surface by bacteria Preferably, said bacteria are selected from *Listeria monocytogenes* and *S. typhimurium*.

Preferably, the use according to the ninth object of the invention is for the sanitization of facilities or machinery intended for processing food products.

According to a further preferred embodiment, the use according to the ninth object of the invention is as a preservative agent of food products, in particular for the prevention and/or treatment of contamination thereof by *Listeria monocytogenes*, in particular for the prevention and/or elimination of bacterial contamination thereof and of the food contained therein.

Preferably, according to a ninth embodiment, said use provides applying at least one peptide according to the invention on the surface and/or inside the body of the food products. Alternatively, said use provides applying at least one peptide according to the invention on the surface of food packaging material.

The nanoparticles are also suitable for the delivery of the peptides to a patient.

Accordingly, a tenth object of the invention are nanoparticles, as described above, for use in the treatment of a bacterial infection in a subject, preferably for use in the treatment of an infection against *Listeria monocytogenes*. An eleventh object of the invention is a method for the treatment of a bacterial infection in a subject, by administering nanoparticles, as described above. Preferably, according to the tenth and eleventh object of the invention, said subject is a mammal, more preferably it is a human.

A twelfth object of the invention is a pharmaceutical composition comprising nanoparticles as described above, optionally in combination with pharmaceutically acceptable excipients or carriers.

Preferably, in the above embodiment of the tenth, eleventh or twelfth object of the invention, the nanoparticles are: natural materials or derivatives (chitosan, dextrane, gelatine, liposomes, alginates, starch), polymer carriers (polylactic acid, poly(cyano) acrylates, polyethileinemine, polycaprolactone), metallic nanoparticles, silica nanoparticles.

EXAMPLES

Example 1—Synthesis of Peptides

The Bac-amp1 and IDR-1018 peptides, having the sequences shown in table 1, were synthesized by solid phase peptide synthesis using the Fluoromethoxycarbonyl (Fmoc) protecting group.

TABLE 1

| Peptide | Sequence |
|---|---|
| Bac-amp1 | VRLIVKVRIWRR-NH2 (SEQ ID NO: 3) |
| IDR-1018 | VRLIVAKVRIWRR-NH2 (SEQ ID NO: 1) |

The Rink-Amide MBHA resin with a degree of substitution of 0.5 mmol/g was used as a solid support. The resin is provided with a "linker", which provides an amide bond and releases the amided peptide to the C-terminus.

At the end of the synthesis, the protecting group was removed by treatment with a solution of 40% (v/v) piperidine in DMF while the detachment from the resin and the removal of the protecting groups on the side chains of the amino acids was obtained by treatment with an acid solution composed of 95% trifluoroacetic acid, 2.5% triisopropylsilane and 2.5% H2O (v/v/v).

After detachment from the solid support, each peptide was precipitated in cold ethyl ether, at −20° C. To recover the precipitate, each sample was centrifuged at 3500 rpm for 5 minutes. The precipitate was dissolved in a mixture of CH3CN/H2O (95:5), frozen and lyophilized.

Example 2—Analysis of Peptide Stability

In a first set of experiments, the stability of Bac-amp1 and IDR-1018 at different temperatures and pH conditions was assessed.

The stability of the Bac-amp1 and IDR-1018 peptides was assessed by studying their secondary structure with Circular Dichroism (CD) spectroscopy in the presence of Sodium Dodecyl Sulfate (SDS) micelles at a concentration of 10 mM to mimic the condition of the cell membrane, in different temperature and pH conditions.

CD assays were performed with a Jasco J-810 Spectropolarimeter equipped with a thermostated cuvette compartment. The samples were loaded into a 0.1 cm-long quartz cuvette (Hellma Analytics) and the spectrum was analyzed in the 190 nm to 250 nm range at temperatures of 15° C. or 90° C. for each sample.

The CD spectra were acquired at a scanning speed of 20 nm/min, and the recorded results represent an average of 5 scans. The spectra at 90° C. were collected at time zero and after 2 hours to evaluate the thermostability of peptides at high temperatures.

The average ellipticity of the residues ($[\theta]$, degrees cm$^2$ dmol$^{-1}$) was calculated using the following equation:

$$[\theta]=100\ \theta/cn1$$

where $\theta$ represents ellipticity (m degrees), c is the concentration (mM) of the peptide, n is the number of residues. The secondary structure was calculated through the DICHROWEB site (Whitmore L and Wallace B A, 2004, Nucleic Acids Research 32: 668-673, Whitmore L and Wallace B A, 2008, Biopolymers 89:392-400, Lobley et al, 2002, Bioinformatics 18:211-212), using three different algorithms (SELCON3, CONTIN-LLe CDSSTR) (Sreerema N and Woody R W, 1993, Analytical Biochemistry 287:252-260; Sreerema N et al, 1999, Protein Science 8:370-380, Provencher S W and Glockner J, 1981, Biochemistry 20:33-37, Van Stokkum I H M et al, 1990, Analytical Biochemistry 191:110-118, Compton L A and Johnson W C, 1986, Analytical Biochemistry 155:155-167, Manavalan P and Johnson W C, 1987, Analytical Biochemistry 167:76-85, Sreerama N et al, 2000, Protein Science 8:370-380) and selecting as a comparison data set the SMP180 protein, which includes a hi number of soluble and membrane proteins (Abdul-Gader A et al, 2011, Bioinformatics 27:1630-1636).

Example 2a—Thermostability Assay 0.1 g/L of Bac-amp1 or IDR-1018 peptide were dissolved in 100 mM sodium acetate buffer at pH 6 and 10 mM SDS.

The prepared samples were incubated for two hours at 15° C. or 90° C. A CD analysis was performed on samples stored at 15° C. and before and after incubation for two hours at 90° C. The results obtained for Bac-amp1 or IDR-1018 are shown in FIGS. 1 and 2, respectively.

Figure 1:
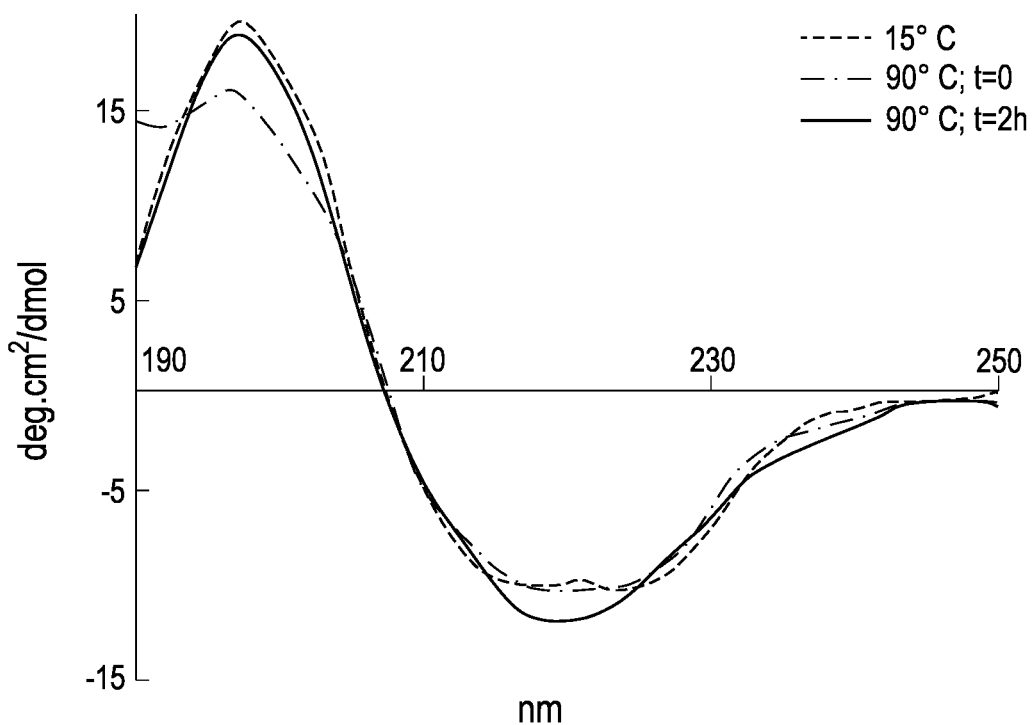

As shown in FIG. 1, all Bac-amp1 CD spectra have two negative bands at 215 nm and 222 nm which indicate a conformational state of the peptide consisting of alpha-helix structures. Furthermore, no significant changes were found in the sample spectra at 90° C., even after 2 hours incubation at this temperature. These data demonstrate that Bac-amp1 maintains its structure unchanged in the range from 15 to 90° C. and is therefore characterized by a high thermostability.

Figure 2:
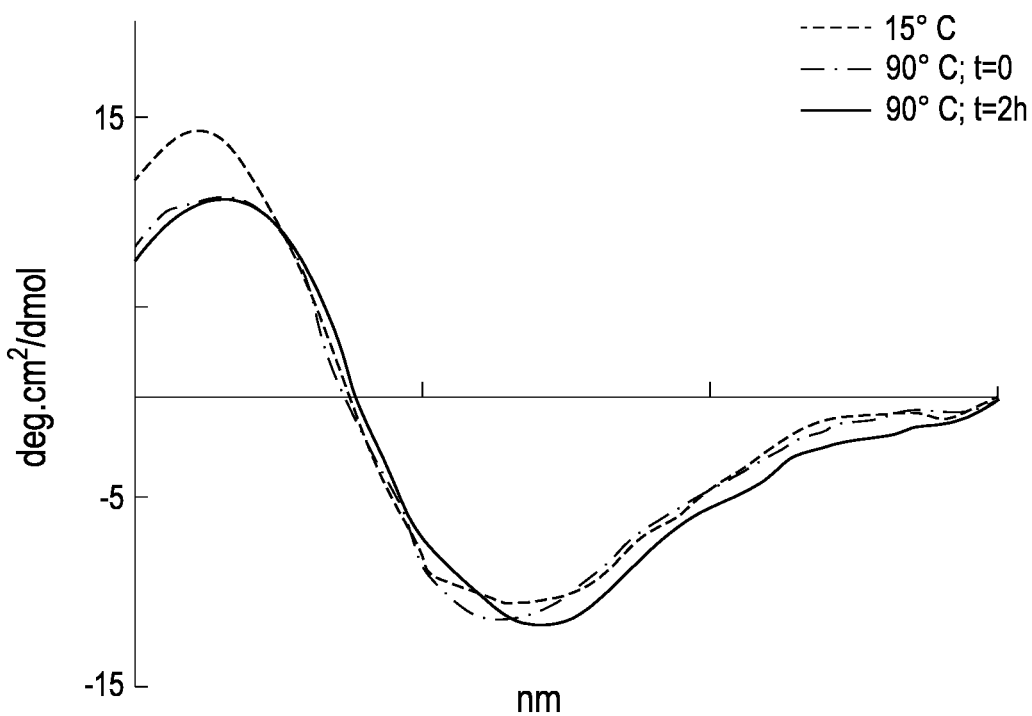

As shown in FIG. 2, all IDR-1018 CD spectra have a singe negative band at about 212 nm which indicates a conformational state of the peptide consisting of mainly beta-sheet structures. Furthermore, also with this peptide, no significant changes were found in the sample spectra at 90° C., even after 2 hours incubation at this temperature. Therefore, also the IDR-1018 peptide is characterized by high thermostability. The different conformation of the two peptides accounts for the different bactericidal activity towards specific microorganisms, discussed below, namely the ability to contrast with different effectiveness the growth of pathogenic bacteria such as *Listeria monocytogenes*.

Example 2b—pH Stability Assay 0.1 g/L of Bac-amp1 or IDR-1018 peptide were dissolved in different solutions at 100 mM concentration, in particular: potassium chloride-HCL (pH 1); glycine-HCL buffer (pH 2); sodium acetate buffer (pH 4 and 6); tris-HCL buffer (pH 8); glycine-NaOH buffer (pH 10); sodium-bicarbonate-NaOH (pH 11). After an hour of incubation at 25° C., samples of each solution containing SDS at a concentration of 10 mM were prepared. The resulting samples and a glycine-HCL buffer sample without addition of SDS were incubated at 37° C. for another 24 hours and analyzed by CD. The results obtained are shown in FIGS. 3 and 4.

In both figures, it is seen that, for both peptides, the samples at pH 2 without addition of SDS show a negative band shifted towards 198 nm which indicates the presence of an unordered "random coil" structure, while all the other samples show an ordered structure, of alpha-helix type for Bac-amp1 and of beta-sheet type for IDR-1018.

Figure 3:
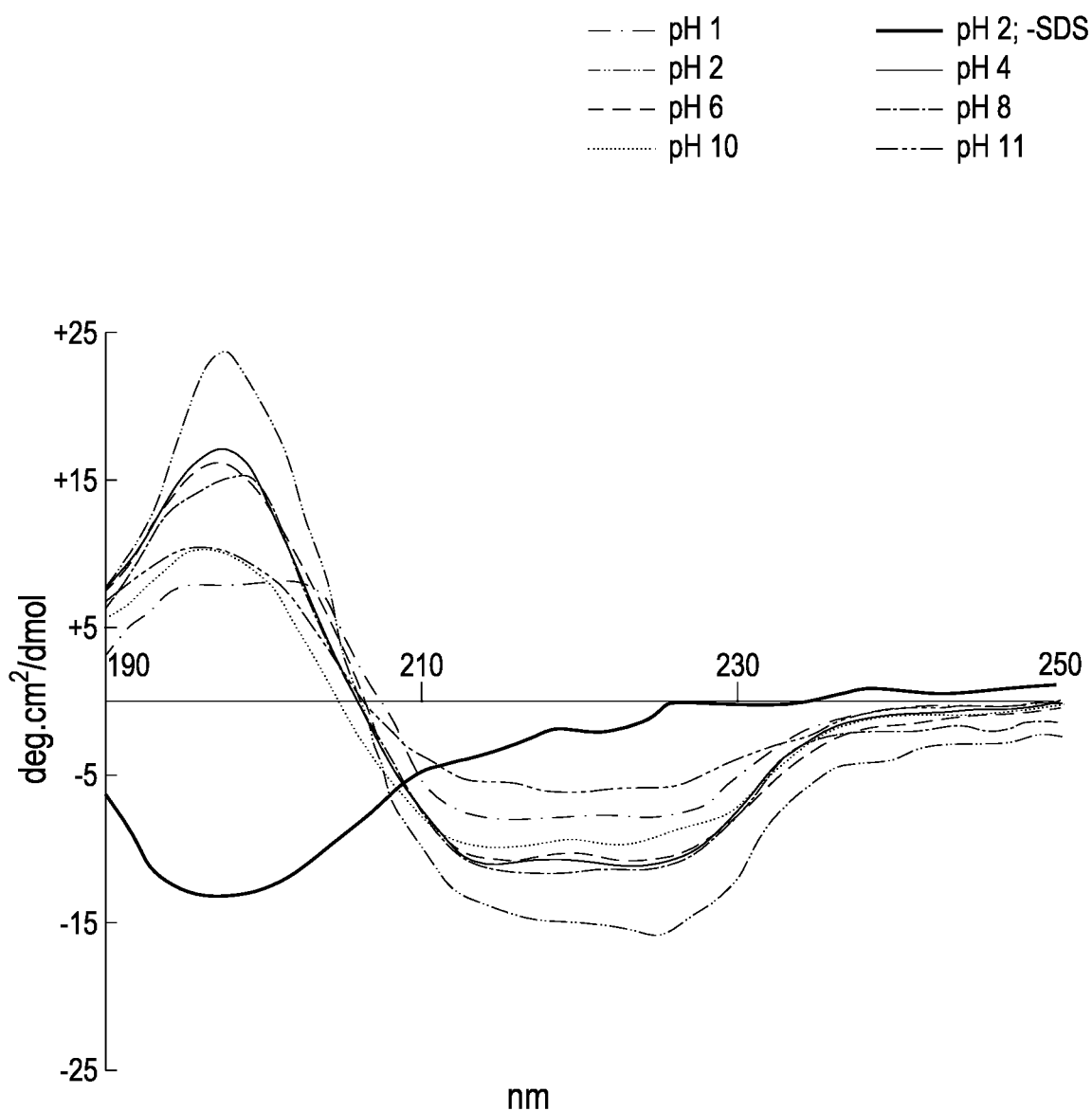

As shown in FIG. 3, all Bac-amp1 CD spectra recorded at different pH conditions in the presence of SDS indicate that the peptide takes alpha-helix conformations, in all the analyzed conditions, to which the peptide functionality is associated.

Figure 4:
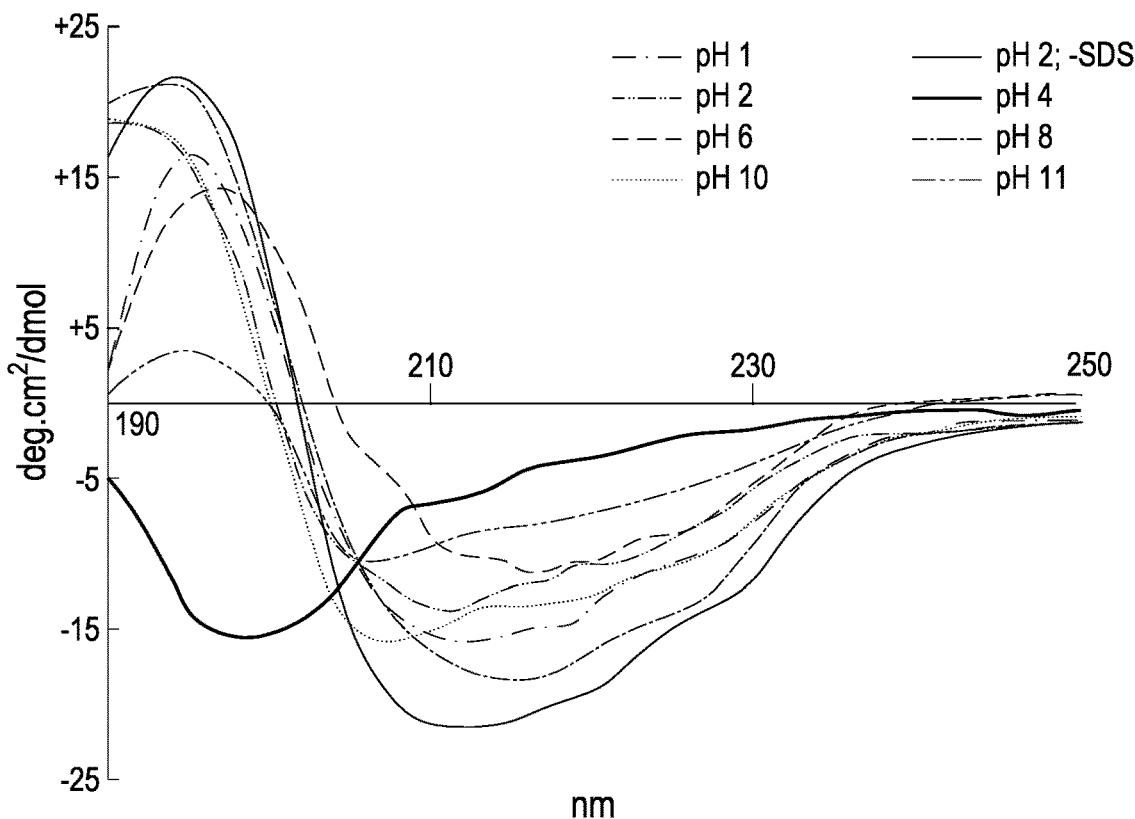

As shown in FIG. 4, the CD spectrum of IDR-1018 recorded at pH 2 without the addition of SDS has a negative band shifted towards 198 nm, which indicates that the peptide under these conditions takes a different conformational state; the CD spectra of this peptide recorded in the presence of SDS at different pH conditions indicate that the peptide takes beta-sheet conformations.

Overall, these results show that the Bac-amp1 peptide maintains its structural integrity over the entire pH range better than the IDR-1018 peptide. In fact, the analysis of the CD spectra of the IDR-1018 peptide in comparison with Bac-amp1 clearly indicates an increase in the percentage of unordered random coil structure in the pH range of 8.0-11.0 for IDR-1018 and in the range of 1.0-4.0 for Bac-amp1. Therefore, the two peptides exhibit a different conformational stability in specific pH ranges and consequently a different functionality, in terms of bactericidal activity since it is strictly dependent on their conformation, whether alpha-helix or beta-sheet.

In the light of these results, the present inventors have shown that the combination of the two peptides ensures bactericidal activity in a wide pH range, which is a feature that finds useful application in the food industry.

Example 2c—Stability Analysis Under Use Conditions

Samples of mozzarella brine were incubated for 24 hours at 4° C. in the presence of Bac-amp1 or IDR-1018 or in their absence (control). The brine was obtained from skimmed, pasteurized kneading water, added with 3-5% NaCl and acidified with lactic or citric acid up to pH 3.8-3.9. The three samples were analyzed by HPLC on a mBondpack C18 reverse phase column (RP).

Figure 5:
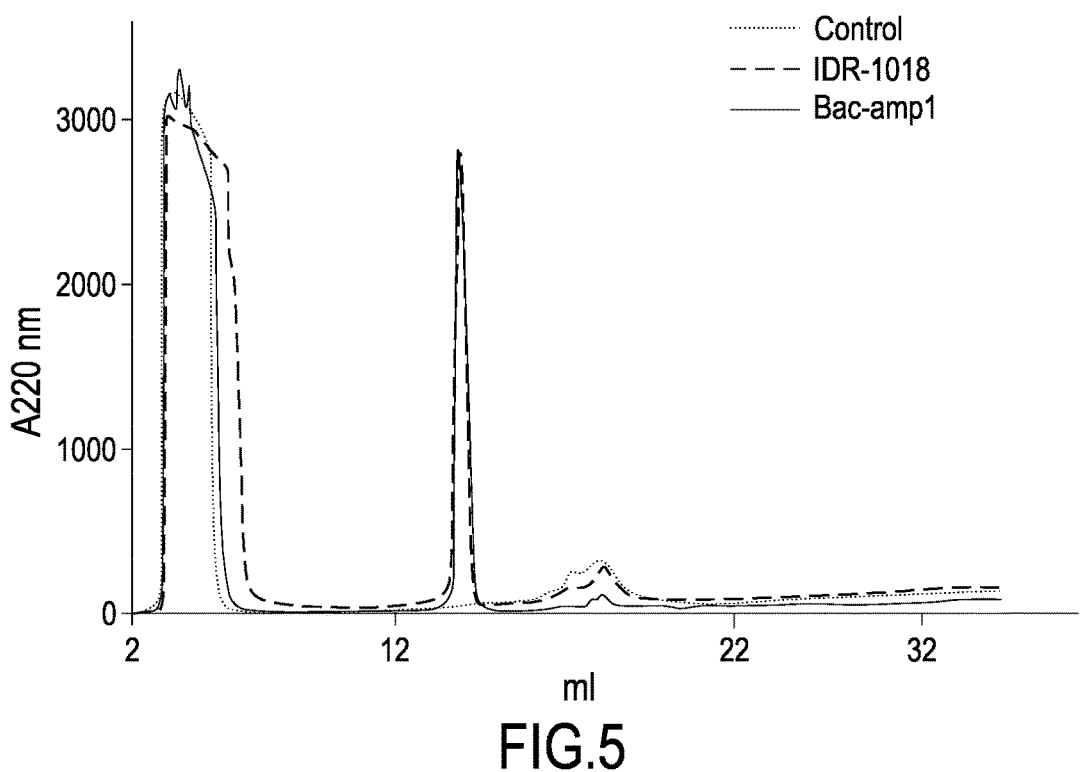

In FIG. 5, a chromatogram obtained for each sample tested is shown; as shown by this chromatogram, neither precipitation nor degradation of the peptides occurred during the incubations, which therefore resulted completely stable in the brine.

Example 3—Bactericidal Activity Assay

The bactericidal activity of the Bac-amp1 and IDR-1018 peptides was evaluated against both Gram+ (*Listeria monocytogenes* and *Staphilococcus aureus*) and Gram− (*Salmonella typhimurium*) pathogenic bacteria.

For the three selected bacterial species, certified and characterized strains were used, indicated in Table 2.

The evaluation of the minimum bactericidal concentration (MBC) was carried out as described in Bilikova et al, (2015, Peptides 68:190-196) and the evaluation of the effective concentration to reduce 50% of the bacterial population (EC50) of the two peptides was carried out with the microdilutions of the broth as described in Wang H X and Ng T B (2003, Peptides 24:969-972).

Standard deviations for triple incubations of each plate and EC50 evaluation were determined using GraphPad Prism version 6.00 (Graph-Pad Software, La Jolla California USA)

*Listeria monocytogenes*

As regards *Listeria monocytogenes*, five field strains were added to the trial (wild strains) SS1 (serotype 4b), SS2 (serotype 4b), SS3 (serotype 4b), SS4 (serotype 4b), SS5 (serotype 1/2c) shown in Table 2. These strains were isolated from 200 samples of food waste, in particular fish products and milk derivatives, obtained from workbenches of food companies. All samples were collected in a context of official controls. Isolation of *Listeria monocytogenes* strains was performed according to the ISO-11290-1 standard. In brief, 25 grams of sample were homogenized (1:10 w/v) in Half Fraser Broth culture medium (AES Laboratoire, Route de Dol, Combourg, France) and incubated at 37° C. for 18 hours. 1 ml of culture broth was transferred to Fraser Broth culture medium (Fraser J A and Sperber W H, 1988, J Food Protect 51(10):762-765) and incubated at 37° C. for 24 hours. Subsequently, the enriched was streaked on ALOA and Oxford agar (Oxoid, Basingstoke, UK) at 37° C. for 24 hours. *Listeria monocytogenes* colonies were identified biochemically with *Listeria* API (BioMérieux, Marcy l'Etoile, France).

For all five field strains obtained, serotyping was performed using protocols which are certified (Pulsed Field Gel Electrophoresis PFGE, PulseNet using the Asci and Apal restriction enzymes) and reported in the Analytical Bacteriology Manual of Food and Drug Administration (FDA) of the United States and through the use of commercial antibodies for somatic (O) and flagellar (H) antigens (Denkan Seiken Co. Ltd, Tokyo, Japan). In particular, the SS1-SS4 strains were found to belong to serotype 4b, which is the most pathogenic and aggressive for humans, responsible for at least 50% of listeriosis cases, while the SS5 strain belongs to serotype 1/2c. A control stock suspension was prepared in which $10^3$ CFU of *L. monocytogenes* (ATCC strain and SS1, SS2, SS3, SS4 and SS5 strains isolated as described above) were inoculated in 10 ml of Half Fraser Broth and serial dilutions (100 to 0.01 µM) of the suspension were performed. 5 mM stock solutions of the two peptides in DMSO were then prepared and serial dilutions (100 to 0.01 µM) were performed in Fraser Broth, which were inoculated with $10^3$ CFU (colony forming units) of *L. monocytogenes* and incubated for 6 hours at 37° C. At the same time, control samples were treated in the same way but without the addition of the two peptides. 50 µl of each bacterial suspension was seeded in different culture plates: blood agar and ALOA (Oxoid, Basingstoke, UK), which were then incubated for 24-48 hours at 37° C. Each dilution series included control plates with bacteria and DMSO alone without the peptide. The assay was performed in parallel with an ATCC strain and with 2 wild strains isolated from sea foods as described above.

*Salmonella typhimurium*

A control stock suspension was prepared in which $10^3$ CFU of *S. typhimurium* (ATCC13311 strain) were inoculated in 10 ml of BPW (Oxoid, Basingstoke, UK). Then, 5 mM stock solutions of the two peptides were prepared and serial dilutions (100 to 1 µM) were performed in BPW, inoculated with $10^3$ CFU of *S. typhimurium* and incubated for 6 hours at 37° C. 50 µl of each bacterial suspension was seeded in petri dishes with blood agar or chromogenic agar (Oxoid, Basingstoke, UK) and incubated for 20 hours at 37° C. Each dilution series included control plates inoculated with DMSO without the peptide and control plates with bacteria alone.

*Staphylococcus aureus*

A control stock suspension was prepared in which $10^3$ CFU of *S. typhimurium* (6571 strain) were inoculated in 10 ml of BPW. Then, 5 mM stock solutions of the two peptides were prepared and serial dilutions (100 to 1 µM) were performed in BPW, which were inoculated with $10^3$ CFU of *S. aureus* and incubated for 6 hours at 37° C. Also in this case, the dilution series included control plates inoculated with DMSO without the peptide and control plates with bacteria only.

50 µl of each bacterial suspension were poured onto petri dishes with blood agar or rabbit plasma fibrinogen agar and incubated for 20 hours at 37° C.

In all the investigated experimental conditions, the plate counting method was used to estimate the bactericidal activity of the peptides. Specifically, the number of colonies grown on plates with agar seeded with bacterial suspensions in the absence or in the presence of individual dilutions of peptides was counted and compared. The standard deviations of the triple incubations of each plate were determined using statistical software.

Figure 6:
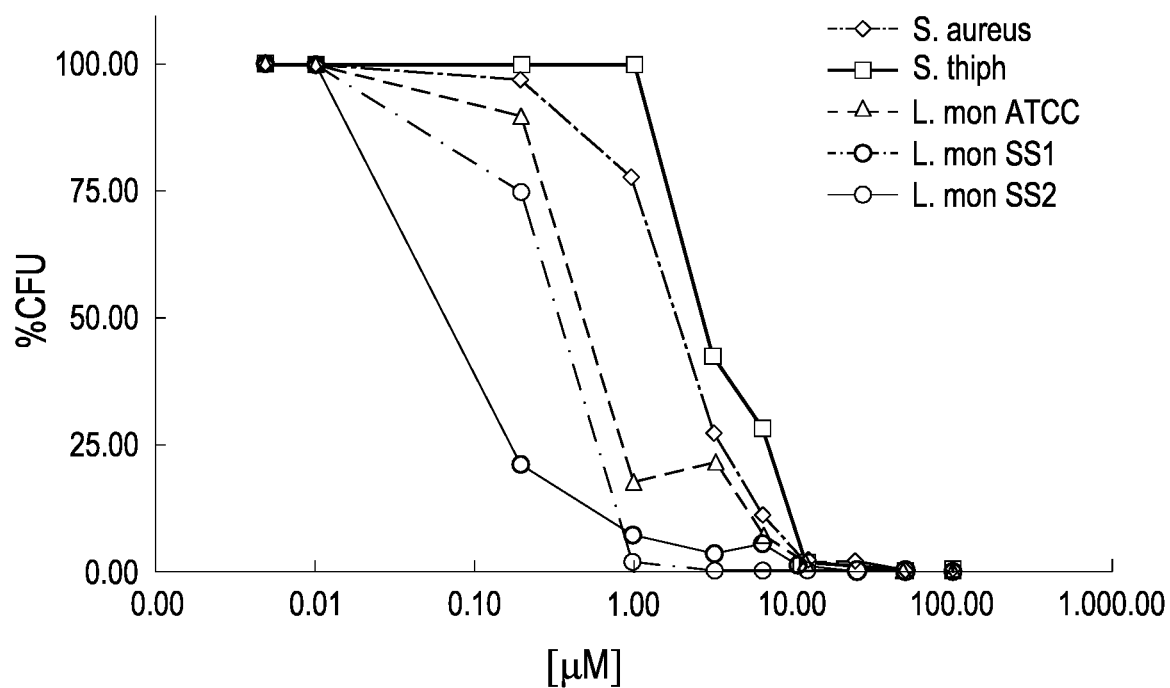

All bactericidal activity assays were performed using 2 log CFUs (when not otherwise specified), which represents a realistic approximation of the levels of contamination that may be contained in fresh food products. FIG. 6 shows the dose-response curve obtained with the Bac-amp-1 peptide against *S. aureus* (NCTC), *S. typhimurium* (ATCC), *L. monocytogenes* (ATCC), *L. monocytogenes* (SS1) and *L. monocytogenes* (SS2).

Based on the dose-response curves obtained with both peptides, the values of EC50 (effective peptide concentration to reduce 50% of the bacterial population present in the medium) against the commercially available bacterial strains (ATCC, NTCC) and *Listeria* field strains (SS1-SS5), for the other three *Listeria* strains isolated from food and work surfaces, the available data allow identifying only the concentration threshold values at which the two peptides are still active (Table 2).

TABLE 2

| Pathogenic species | EC50 IDR-1018 | EC50 Bac-amp1 |
|---|---|---|
| *S. aureus* (NCTC) | 1.58 µM | 1.66 µM |
| *S. thyphimurium* (ATCC) | 3.12 µM | 2.83 µM |
| *L. monocytogenes* (ATCC) | 0.22 µM | 0.55 µM |
| *L. monocytogenes* (SS1) | 0.69 µM | 0.28 µM |
| *L. monocytogenes* (SS2) | 0.40 µM | 0.08 µM |
| *L. monocytogenes* (SS3) | <25 µM | <1 µM |
| *L. monocytogenes* (SS4) | <25 µM | <1 µM |
| *L. monocytogenes* (SS5) | <25 µM | <1 µM |

The data reported in Table 2 show that for both peptides there is a powerful bactericidal activity against *L. monocytogenes* compared to that recorded against *S. aureus* and *S. typhimurium* strains, which is of moderate magnitude.

In fact, both peptides show an EC50 value of less than 0.7 µM on all *Listeria* strains. Furthermore, while the IDR-1018 peptide shows a more potent activity against the commercial *Listeria* strains, the Bac-amp1 peptide seems to have a particular action specificity towards the 5 field strains, with values of EC50 included between <1 µM and 0.28 µM. These results suggest that in the case of Bac-amp1 there is a precise mechanism of antimicrobial action against *Listeria* which involves translocation of the bacterium through the membrane b interact and inhibit specific intracellular targets involved in vital metabolic processes.

This activity of the Bac-amp1 peptide represents a very relevant datum from an applicative point of view if we consider that generally, microbial strains isolated from the environment ad/or food show adaptation or resistance to antibiotics and disinfectants, probably due to the presence of mobile genetic elements carrying resistance genes or altered permeability of the bacterial cell wall.

Example 4—Antibiofilm Activity Assay

The antibiofilm activity of the Bac-amp1 and IDR-1018 peptides was tested by analyzing their ability to inhibit the formation of bacterial biofilms of *L. monocytogenes*.

Since it is known that the antibiotic activity of antimicrobial agents is strongly dependent on the experimental approach, which could favour the inhibition of biofilms and overestimate their real effectiveness, in the present study the assessment of the ability of such peptides to counteract the formation of bacterial biofilms was carried out on steel discs, an inert material widely used in the food industry.

Example 4a—Antibiofilm Activity Assay with Crystal Violet Staining

The ability of peptides to prevent the formation of *L. monocytogenes* biofilms was determined according to the microplate assay described in G. Di Bonaventura et al. (2008, J Appl Microbiol 104(6):1552-61) with some modifications.

*L. monocytogenes* cultures (ATCC7644 and EURL12MOB098LM) were prepared by inoculating Brain Heart Infusion Broth broth (Sigma-Aldrich, City and State) at 37° C. up to a logarithmic growth phase. 10 ml of bacterial suspension were then centrifuged the cell pellet was washed in PBS and diluted in BHI broth, reaching the concentration of about $10^3$ CFU/ml of standardized inoculum.

The biofilm formation assays were conducted using as target surfaces the Aisi 304 stainless steel discs having a diameter of 14.5 mm (SS) used in the food industry as food contact surfaces. The discs were placed on 24-well Falcon tissue culture plates, (Thermo Fisher Scientific Inc., Waltham, Massachusetts, USA), with flat bottom and lid. Before use, the stainless steel discs were immersed in 10% acetone and left under weak stirring at room temperature for 30 min. After washing in ultrapure sterile water, the discs were incubated in ethanol ≥99.8% for 10 minutes under weak stirring and then washed in ultrapure sterile water, dried, packaged and sterilized at 121° C., 1 atm for 15 minutes.

In each set of experiments, 600 μl of standardized inoculum in the presence or absence of each of the peptides at the concentration of 12.5 μM, 25 μM or 50 μM were added to 24-well culture plates containing the previously treated stainless steel materials. BHI Broth was used as a negative control. The plates were incubated at 37° C. for 72 hours under static conditions. The cell count of *L. monocytogenes*, according to the ISO 11290-2:98 method. After incubation, the SS discs were washed three times with PBS and placed in a new plate to dry at 60° C. for 1 hour. 1 ml of 0.2% crystal violet in 95% ethanol was added to each well to stain the bacterial cells adhered to the surface of the SS discs. After weak stirring for 15 minutes, the SS discs were washed three times with sterile water and then transferred to a new plate to dry at 37° C. for 1 hour. Quantitative analysis of biofilm production was performed by adding 1 ml of 33% acetic acid, which removes the dye from the adhered cells. 200 μl of the obtained solution were transferred to a microplate and the crystal violet level (OD) was measured at 492 nm.

The amount of bacterial biomass for each incubation condition was represented by "box plots" diagrams; the points outside the box were considered as anomalous values (outliers). Statistical significance tests were performed by applying non-parametric variance analysis (Kruskal-Wallis test) followed by multiple pairs comparisons using Dunn's test with Bonferroni correction ($p<0.05$). Statistical assays were performed using MICROSOFT® EXCEL 2000/XL-STAT©-PRO, a tool for statistical analysis in the spreadsheet programme developed by Microsoft.

Figure 7:
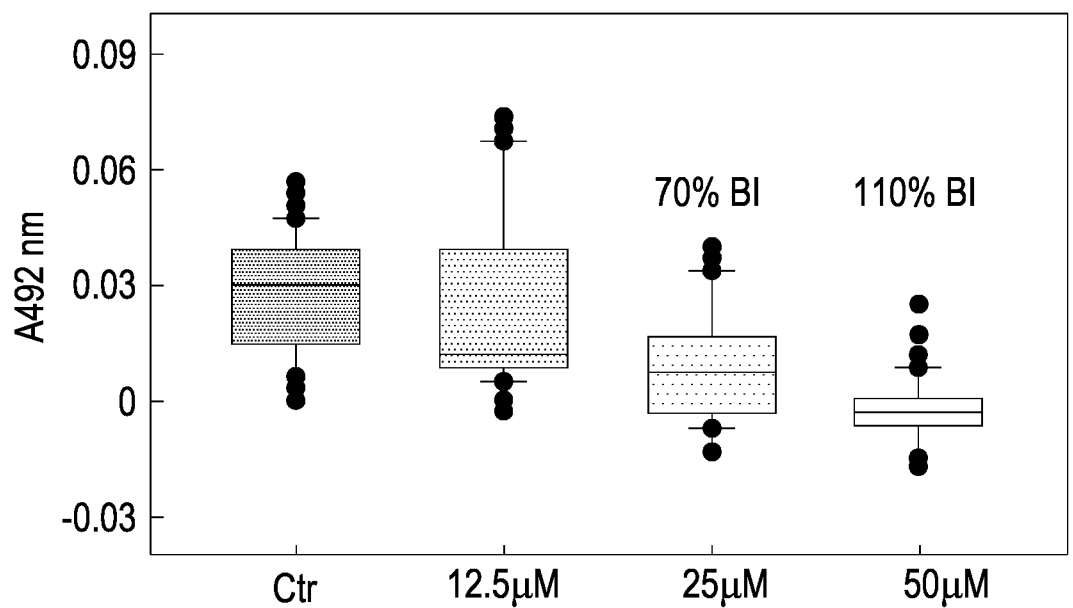

As shown in FIG. 7, the Bac-amp1 peptide showed a significant antibiotic activity with a reduction of 70%-80% microbial biomass at concentrations of 20-25 μM and 100% at concentrations of 25-50 μM corresponding to the value of $MBIC_{100}$ (minimum biofilm inhibiting concentration).

Figure 8:
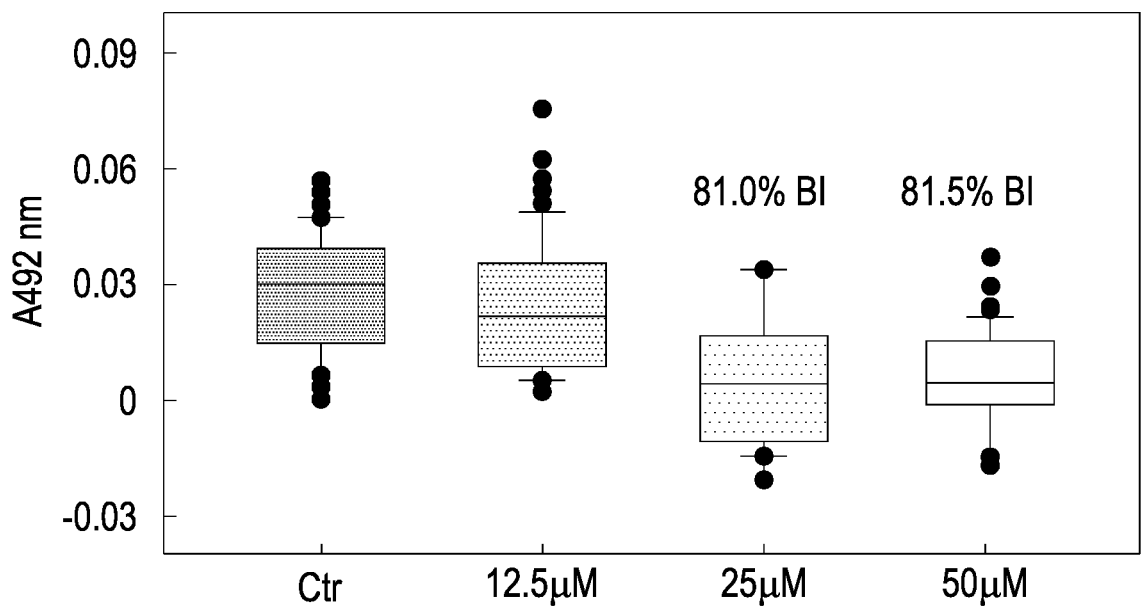

As shown in FIG. 8, the IDR-1018 peptide, as opposed to Bac-amp1, does not 100% inhibit the formation of bacterial biofilm in any of the experimental conditions adopted, reaching a maximum inhibition of 81.5% at the 50 μM concentration.

These results show that the Bac-amp1 peptide is capable pf totally inhibiting the formation of antibiofilm by *Listeria*, while IDR-1018 has a weaker antibiofilm activity.

These data also suggest that the conformation adopted by the Bac-amp1 peptide is more suitable than that of the IDR-1018 peptide in preventing the growth of the biofilm produced by *Listeria monocytogenes*.

Example 4b—Antibiofilm Activity Assay with SEM

The activity of the Bac-amp1 and IDR-1018 peptides on *L. monocytogenes* biofilms was further investigated by scanning electron microscopy (SEM).

Specifically, in this example the three-dimensional biofilm architecture, developed on stainless steel materials, was studied.

The Aisi 304 stainless steel discs with a diameter of 14.5 mm (SS) were treated with 600 μl of standardized inoculum in the presence or absence of each of the peptides at the concentration of 25 μM or 50 μM, or with control medium, according to the same method of Example 4a and repeatedly washed in sterile PBS to remove planktonic cells and fixated on a new plate with 1 ml of Karnovsky fixative containing 5% glutaraldehyde, 4% paraformaldehyde in buffer 0.064 M (Electronic Microscopy Science, Hatfield, PA, USA) for 1 hour at 4° C. Thereafter, the samples were washed in 0.1 M cacodylate sodium buffer at pH 7.4 (Electronic Microscopy Science, Hatfield, PA, USA) and the fixated cells were dehydrated in a series of aqueous acetone solutions at different concentrations, in particular 25%, 50%, 75% and 100%. The samples were glued onto polished aluminium sample holders (Electronic Microscopy Science, Hatfield, PA, USA) and uniformly vacuum coated with a 20-nm thick gold layer with the K950 high-vacuum Turbo Evaporator and a K 350 coupling (Emitech Ltd, Ashford, UK). The coated samples were examined at the JEOL 6700 FEG Field Emission Electron Microscope (SEM Jeol, City and State) with magnification from 1000× to 5000×. For each sample, a number of images (5-10), acquired as electronic images were randomly analyzed.

It was observed that the treatment with Bac-amp1 significantly reduces the formation of biofilm already at 25 μM while the best result is observed at 50 μM.

FIG. 9 shows microscopic images showing the effect of the Bac-amp1 peptide at a concentration of 50 μM on biofilm formation.

Figure 9A:
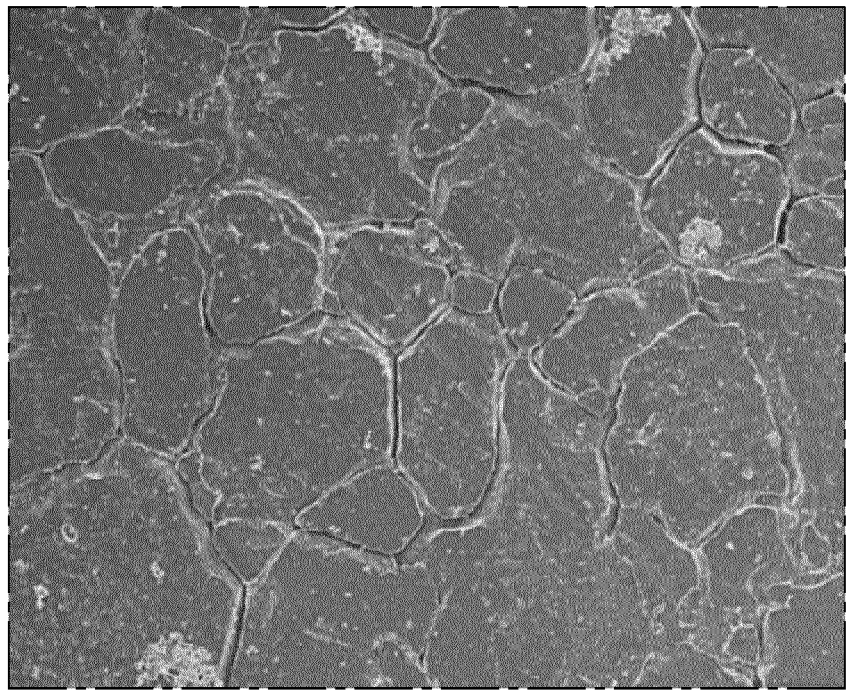
Figure 9B:
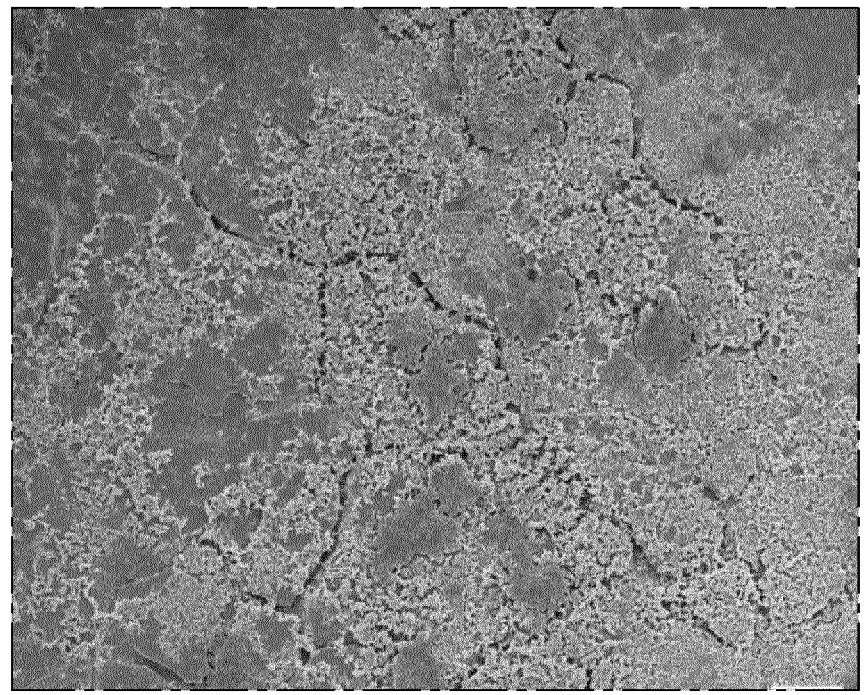

As seen in FIG. 9a, the 1000× image of the samples treated with Bac-amp1 shows cells that are more rare and scattered than those of untreated control samples, whose image is shown in FIG. 9b.

Figure 9C:
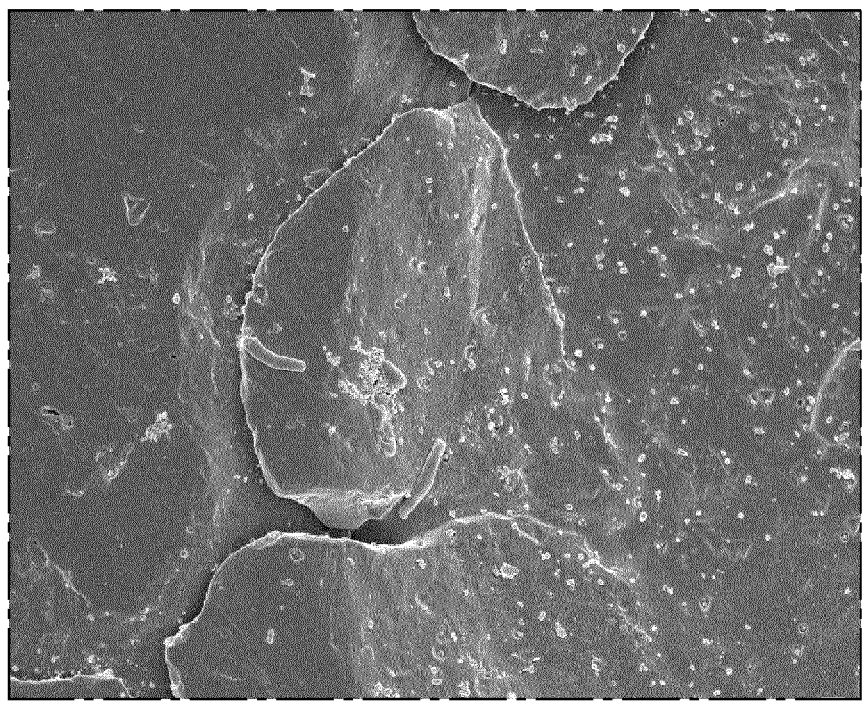
Figure 9D:
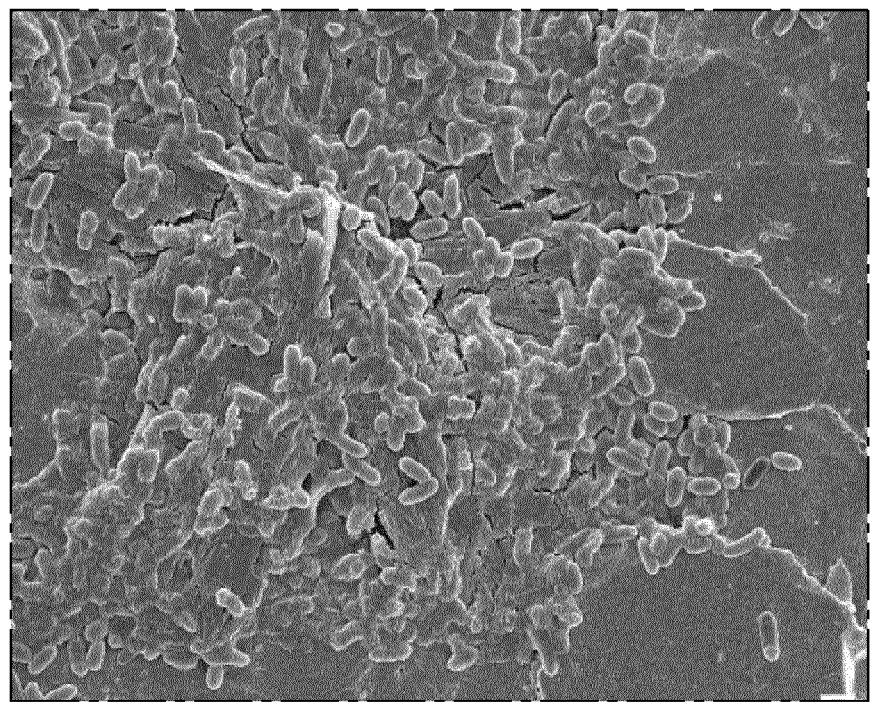

As shown in FIG. 9c, the 5000× image of the samples treated with Bac-amp1 shows the near absence of cells, which instead are present in the untreated control samples, whose image is shown in FIG. 9d.

FIG. 10 shows microscopic images showing the effect of the IDR-1018 peptide at a concentration of 50 μM on biofilm formation.

Figure 10A:
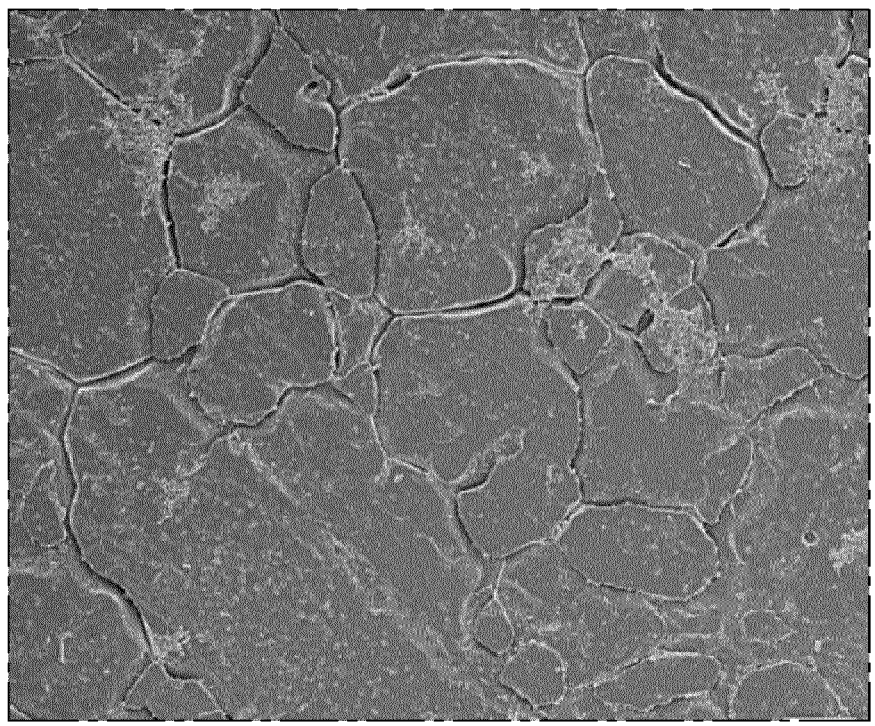
Figure 10B:
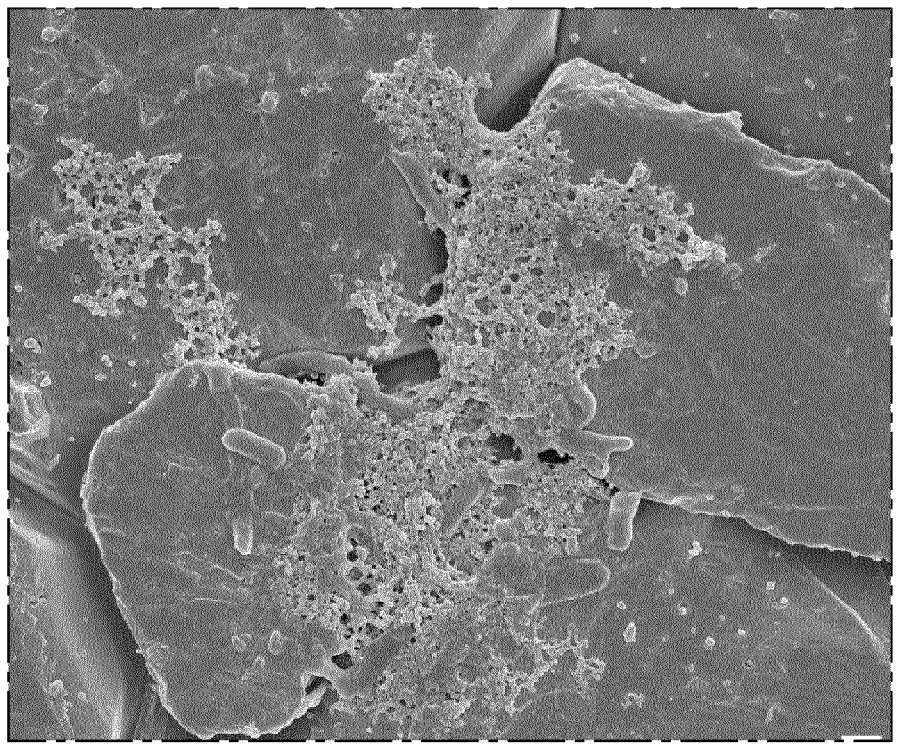

As seen in FIG. 10a, the 1000× image of the samples treated with IDR-1018 shows a greater number of cells compared to the 1000× image of the samples treated with Bac-amp1, shown in FIG. 9a Furthermore, as can be seen in FIG. 10b, the 5000× image of the samples treated with IDR-1018 shows a greater number of cells compared to the 5000× image of the samples treated with Bac-amp1, shown in FIG. 9c.

These results confirm that the Bac-amp1 peptide is capable of exerting its bactericidal activity also on biofilms and has a capacity to inhibit the formation of biofilm produced by *L. monocytogenes* that is clearly superior to that of the IDR-1018 peptide.

Example 5—Bactericidal Activity Assay on Supports Functionalized with Bac-amp1

A solid support consisting predominantly of silicon oxide ($SiO_2$), hereinafter referred to as SOS, was immersed in a solution of sulfuric acid ($H_2SO_4$) and hydrogen peroxide ($H_2O_2$) in the volume proportion of 4:1 at room temperature for thirty minutes, in order to create the Si—OH groups on the surface of the SOS, after which the sample was washed in demineralized water. Thereafter, the sample was immersed for sixty minutes at room temperature in an anhydrous toluene solution containing 5% by volume of aminopropyltritoxysilane as a silanizing agent, so as to replace the thermodynamically stable Si—OH bonds with the much stronger Si—C ones. At the end of the incubation, the sample was placed on a hot plate at 100° C. for ten minutes. The sample was then incubated in a solution containing 150 µl of bis-succininimide suberate (a bifunctional group capable of covalently binding the Bac-amp1 peptide through the N-terminal end) at a concentration of 1.6 mM dissolved in PBS solution (0.1 M pH=7.4) at 4° C. for 5 hours.

The functionalized material (SOSF) with Bac-amp1 was incubated with cultures of *L. monocytogenes* ($3 \times 10^3$ CFU/ml) in a suitable container, and the bactericidal activity of the immobilized peptide was evaluated by means of vital colony counts on culture samples taken at different time intervals. The same analysis was performed using non-functionalized support (KSOS) as a control.

Figure 11:
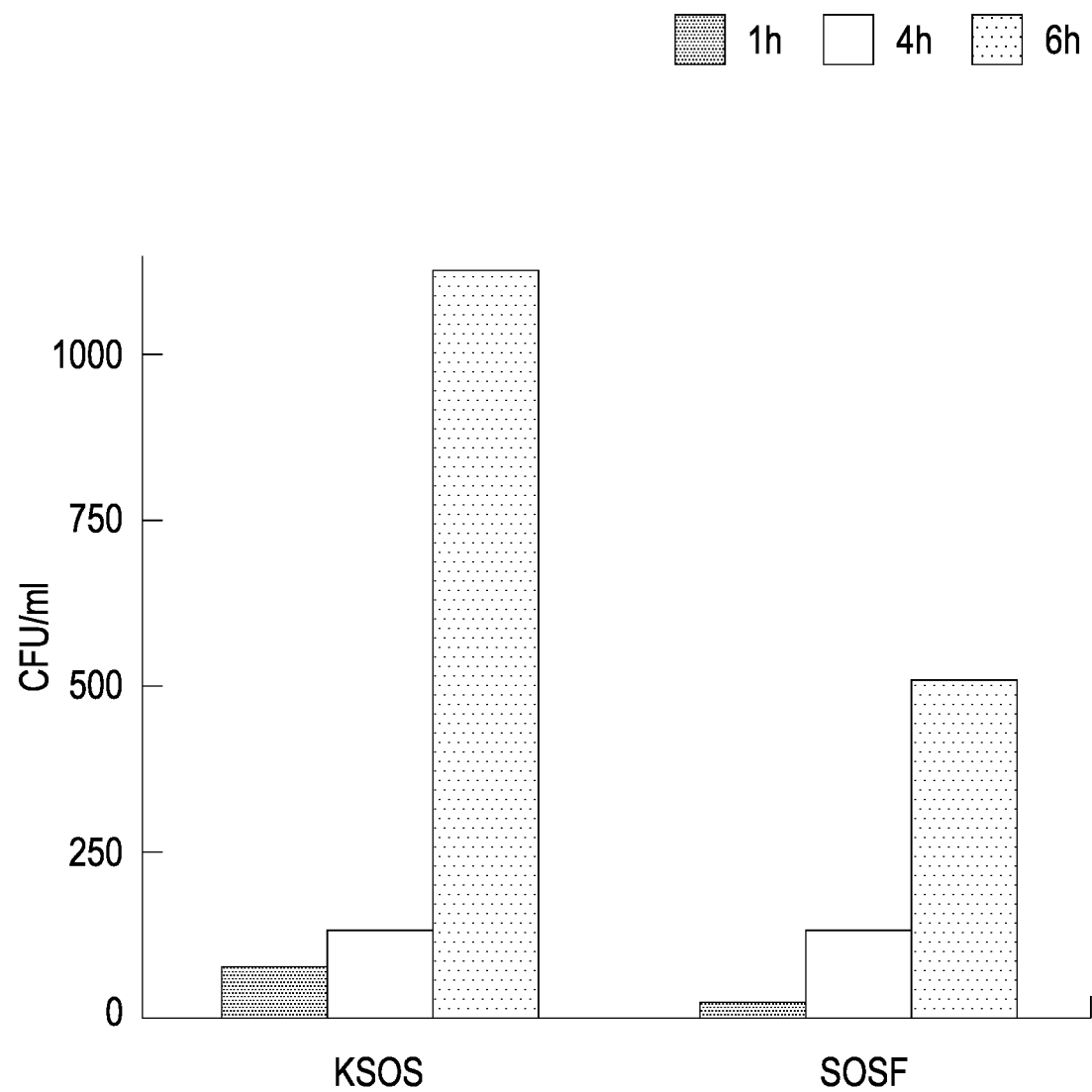
FIG. 11 shows the number of colony-forming units measured following plate seeding of samples of *L. monocytogenes* incubated for different time intervals, 1 h, 4 h, and 6 h, with a material functionalized with the Bac-amp1 peptide (SOSF) or with the same material in the absence of functionalization with the peptide (KSOS), as described in Example 5.

The data shown in FIG. 11 indicate a significant decrease of the CFU in the presence of the functionalized material, observable after 6 hours of incubation. The results obtained support the production of "ad hoc" functionalized materials for applications in different industrial sectors.

Example 6—Preparation of Cold Nanospheres Conjugated with IDR-Bac-amp1

Figure 12:
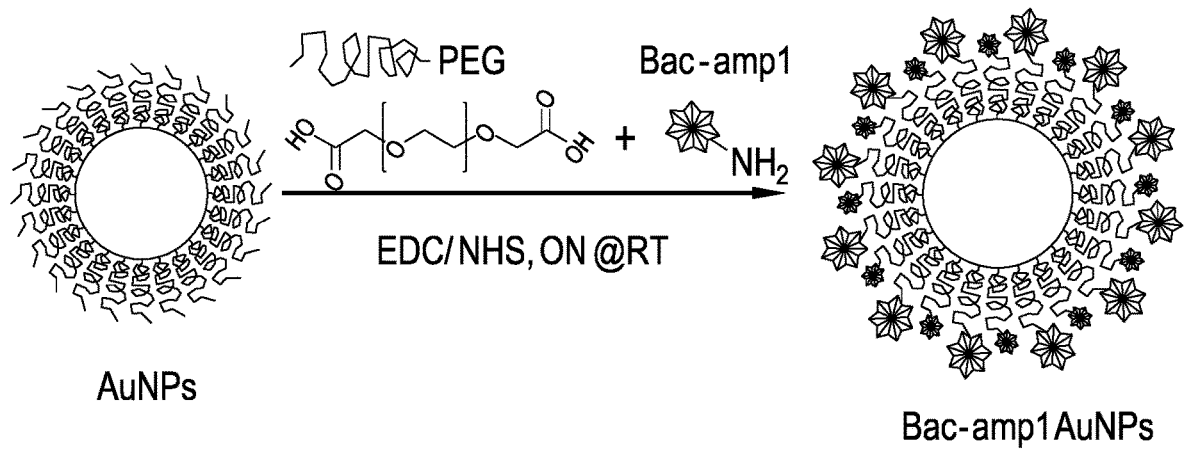
FIG. 12 shows a schematic view of the preparation of gold nanoparticles covalently linked to peptide Bac-amp1 (Au-NPs-Bac-amp1), as described in Example 6.

The chemical reactions leading to the formation of peptide conjugated gold nanospheres are schematically illustrated in FIG. 12.

In details, PEG-stabilized gold nanoparticles were synthetized from chloroauric acid (0.25 mM, 25 mL; HAuCl4 3H2O, Sigma-Aldrich, USA) by mixing poly(ethylene glycol)diacid (0.25 mM, 0.25 mL, PEG-diacid, Sigma-Aldrich, USA) and sodium tetrahydridoborate (0.01 M, 20 mL, NaBH4, Sigma-Aldrich, USA) as surfactant and reducing agent, respectively, as described in Spadavecchia et al, *Analyst* 2014, 139, 157-164 (doi: 10.1039/C3AN01794J).

The formation of the PEG-stabilized gold nanoparticles was observed as an instantaneous colour change of the solution from pale yellow to bright red after addition of the reducing agent. The reaction mixture was centrifuged at 15.000 rpm for 30 minutes for three times and then the supernatant discarded. The resulting pellet of gold nanoparticles was re-suspended in 20 ml of MilliQ-water.

As shown in FIG. 12, the carboxyl groups of PEG-stabilized gold nanoparticles obtained were covalently conjugated to the N-amine groups of Bac-amp1 (0.125 or 0.030 mM) by reaction with 1-ethyl-3-[3-dimethylaminopropyl] carbodiimide hydrochloride and N-hydroxysuccinimide (EDC 5 mM/NHS 2.5 mM, Sigma-Aldrich, USA), under stirring overnight at room temperature as described in Terracciano, at al, *Nanoscale* 2015, 7, 20063-20074. (doi: 10.1039C5NR05173H).

The site-specific addition of the carboxyl group of PEG at the N-terminus of the peptide was controlled by lowering the pH at which the PEGylating reaction takes place. Indeed, acid values of pH selected the reaction between PEG-COOH and the N-terminus, since its pKa is equal to 2.18 while the pKa of the amino group on the side chain of lysine residue, which could be also an attractive target for EDC/NHS conjugation chemistry, is equal to 8.95.

After the conjugation with Bac-amp1 peptide, the gold were washed twice with MilliQ-water and re-suspended in MilliQ-water.

Example 7-Characterization of Bare and Bac-amp1-Modified Acid Nanoparticles

Transmission electron microscopy (TEM) was used to study morphology of the nanospheres obtained in Example 6 before and after conjugation with 125 µM Bac-amp1. To this aim, 1 ml of the sample was centrifuged for 30 min at 15 000 rpm and the supernatant discarded. The solid portion was re-dispersed in 1 ml of MilliQ-water and 10 µL of NPs dispersion were placed on a TEM copper grid with a lacy carbon film, dried at room temperature and then observed by a FEI Tecnai G2 Spirit BT TEM at an accelerating voltage of 100 KV.

Hydrodynamic diameter (size) and ζ potential (surface charge) of the nanoparticles dispersed in water (pH 7) were measured by dynamic light scattering (DLS) using a Zetasizer Nano ZS (MalvernInstruments, Malvern, UK) equipped with a He—Ne laser (633 nm, fixed scattering angle of 173°, room temperature 25° C.). 1 mL of NPs solution was centrifuged for 30 min at 15 000 rpm and re-dispersed in MilliQ-water before each measurement. Absorption spectra of bare and modified gold nanoparticles (1 mL) were recorded using a V-570 UV/VIS/NIR Cary 100 (Agilent) spectrophotometer from Jasco Int. Co. Ltd, Tokyo, Japan in the range between 300 and 900 nm.

DLS was used to quantify the average diameter of bare nanoparticles in $8 \pm 2$ nm, while Bac-amp1-HAuNPs were $16 \pm 4$. The surface charge was −26 mV, before 125 µM peptide conjugation, due to exposure of —COOH PEG groups, and +27 mV after coupling due to positive aminoacids of Bac-amp1, which has 4 positive net charges.

The Bac-amp1 nanoparticles colloidal solution demonstrated exceptional chemical stability over time: the first batch was synthetized at the end of June and even if stored on bench at room temperature, it worked in experiments in December; further control analyses (by DLS and CD) confirmed that in March size and conformational parameters did not change.

TEM imaging showed well-dispersed nanoparticles with average size of $13 \pm 5$ nm (FIG. 1 (*d*)) and $14 \pm 7$ nm (FIG. 1 (*e*)) after Bac-amp1 grafting; these data were in accord to that of DLS within their experimental errors. Despite the quite high negative surface charge and the high stability in solution, the Bac-amp1 nanoparticles revealed some tendency to aggregate after drying. This effect was probably due to peptide clustering.

Example 8—Functionalization Yield Analysis

Reverse phase high performance liquid chromatography (RP-HPLC) was used to analyze the yield of functionalization of the nanospheres obtained in Example 6 by means of both a direct and an indirect method.

Three different solutions were prepared for analysis.

Once functionalization was completed, the reaction mixture was centrifuged at . . . .

The supernatant solution after centrifugation, containing the unbound peptide, was recovered (unbound Bac-amp1).

The peptide bound nanoparticles separated from the supernatant were treated with 50% (v/v) trifluoroacetic acid (TFA, Sigma-Aldrich, USA), under stirring overnight at room temperature, as described in Solid-phase peptide synthesis, Advances in Enzymology and Related Areas of Molecular Biology, Volume 32 (2006): 221-296. The supernatant containing the bound peptide cleaved from the nanoparticles was recovered after centrifugation at 15000 rpm for 30 min at 10° C.

Samples of the two solutions obtained above were analyzed in parallel by RP-HPLC, together with a reference solution with the initial peptide concentration (125 µM) used for the functionalization (Bac-amp1).

For the analyses, 200 µl of sample were injected over a µBondapak C18 reverse-phase column (3.9×300 mm, Waters Corporation) connected to a UFLC system (Shimadzu) using a linear gradient of 0.1% TFA in acetonitrile from 5% to 95%. All measurements were carried out in triplicate.

The absorbance curves obtained for the three samples is shown in FIG. 13, which shows the absorbance curve of the reference solution (Bac-amp1), for the supernatant solution after cleavage of the peptide from the surface of the nanoparticles (bound Bac-amp1) and for the supernatant solution at the end of the functionalization reaction (unbound Bac-amp1).

In the direct method, the yield of the functionalization reaction expressed as a percentage was measured by comparing the peak area obtained from the supernatant of the cleavage reaction with the peak area obtained from the reference solution.

These data demonstrate that no more than 9.0±1.0% of peptide was covalently conjugated to the gold nanoparticles surface.

In order to further validate the result, the bound peptide was also estimated by means of an indirect method, where the peak area of the peptide not attached to the nanoparticles was calculated and compared with the peak area obtained from the reference solution. In contrast to the direct approach, in this case the peak area quantified the amount of the peptide not bound to nanoparticles surface. The results demonstrated a similar trend to those obtained by direct quantification method, with a coupling yield equal to 11.0±1.0%.

On average, we therefore assumed that 10% of the initial peptide concentration (125 µM) was covalently bound on the gold nanoparticles, resulting in approximately 12.5 µM peptide concentration in the Bac-amp1 coupled nanoparticles solution.

In order to test the effect of the Bac-amp1 concentration on the immobilization yield, which is one of the most critical parameters to achieving the formation of stable and active nanoparticles, different amounts of peptide were tested to optimize the coupling reaction conditions. As shown in FIG. 14, it was evident that the most suitable coupling conditions for improving the immobilization yield were obtained with a peptide concentration of 125 µM. Indeed, when a lesser amount of Bac-amp1 was added in the mixture, the coupling reaction resulted less effective as compared to 125 µM concentration of peptide and it was also accompanied by precipitation of nanoparticles, probably due to the fact that the surface was not completely covered by the peptide thus favoring their agglomeration. Similarly, further increase in the concentration did not determine significant changes in the conjugation yield of the peptide to gold nanoparticles. Hence, 125 µM was considered the concentration of saturation and the most suitable for further experimentations.

Example 9—Antimicrobial Activity of Bac-amp1 Coupled Nanoparticles

The bactericidal efficacy of the functionalized gold nanoparticles prepared in Example 6 was determined against *L. monocytogenes* (LM2 food-isolated strain) and *S. Typhimurium* (ATCC 13311 strain) bacteria, which allowed the evaluation of the minimal bactericidal concentration (MBC50), corresponding to the lowest peptide concentration able to cause at least 50% reduction in the number of viable bacteria on agar plates.

*L. monocytogenes* and *S. Typhimurium* were grown at 37° C. in Half Fraser (Biorad-Italia) and BPW (Biomerieux-Italia) broths, respectively.

In one set of experiments, cultures with different dilutions of *L. monocytogenes* cells (ranging from $15\times10^2$ to $15\times10^5$) or *S. Typhimurium* cells (ranging from $15\times10^1$ to $15\times10^3$) were incubated with a fixed concentration of Bac-amp1 (0.16 µM) coupled to nanoparticles (Au-NPs-Bac-amp1 plates) or non-functionalized gold nanoparticles (Au-NPs plates).

Data were determined by numbering the surviving colony forming units (CFU) in the Au-NPs-Bac-amp plates and in the Au-NPs plates and were expressed as percent decrease in the number of CFU with respect to the initial number of CFU. The error bars represent the standard deviation (SD) from the mean for a triplicate experiment (n=3).

The results obtained with *L. monocytogenes* bacteria are shown in FIG. 15 and with *S. Typhimurium* cells in FIG. 16.

As can be seen from FIG. 15, Bac-amp1-loaded nanoparticles exerted a strong bactericidal activity against the food-isolate *L. monocytogenes* strain LM2, causing a significant reduction in the number of CFU, as compared to both uncoupled HAuNPs. Indeed, 99.8% and 99.9% inhibition in bacterial growth was observed in plates inoculated with $10^4$ and $10^5$ bacterial concentrations, respectively, whereas the extent of inhibition increased up to 100% with $10^2$ CFU/ml inoculum. In this case, the enhanced mechanism of the antimicrobial agent was also attributable to an intrinsic effect of the uncoated gold nanoparticles, which elicited 96.2% inhibition in growth of gram-positive bacteria, probably due to the release of gold ions from the nanoparticle core.

The bactericidal properties of the developed Bac-amp1 coupled nanoparticles, were also tested against *S. typhimurium* one of the most dangerous foodborne pathogens chosen as model of gram-negative bacteria.

As shown in FIG. 16, only the loaded nanoparticles led to a pronounced reduction in the number of viable bacterial cells (99.91%) of *S. typhimurium* when 0.16 µM in the $10^3$ bacterial concentrations, in contrast with that observed against a lower cell density ($10^1$ bacterial concentration), in which the uncoated nanoparticles exhibited 30% antimicrobial activity.

These results demonstrated that the tethered peptide after conjugation to the nanoparticles shows an excellent ability in killing both Gram-negative and Gram-positive bacteria even at infectious doses of foodborne pathogens causing outbreaks, thus suggesting a potentially application of the coupled nanoparticles in a wide array of industrial sectors. On the basis of these results, a starting inoculum of approximatively $15 \times 10^4$ CFU/ml, at which no lethal activity was displayed by the bare HAuNPs, was found to be optimal for the assessment of HAuNPs-Bac-amp1 antibacterial activity in a dose-dependent manner.

Thus, in another set of experiments, the activity of Bac-amp1 coupled nanoparticles was determined incubating $15 \times 10^4$ CFU/mL (colony forming units/mL) of *Listeria* with increasing concentrations, ranging from 0.10 µM to 0.58 µM, of coupled nanoparticles (Au-NPs-Bac-amp1 plates), non-functionalized gold nanoparticles (Au-NPs plates) or free peptides (Bac-amp1 plates) for 6 h at 37° C. The number of viable colonies for the different plates at each concentration tested were counted.

As shown in FIG. 18, both Au-NPs-Bac-amp1 plates (grey bars) and Bac-amp1 plates (white bars) showed a dose-dependent bacterial cell death. However, a significantly higher killing activity, was measured when the peptide was bound on gold particles.

These data demonstrate that conjugation of Bac-amp1 with gold nanoparticles not only does not disrupt the activity of the antimicrobial peptide but, surprisingly, potentiates its antimicrobial activity.

The stability of the antimicrobial activity of the conjugated nanoparticles over time was evaluated by measuring the bactericidal activity of 0.16 µM coupled nanoparticles against $10 \times 10^4$ CFU/mL (colony forming units/mL) of *Listeria monocytogenes*, at different time intervals. The result obtained show that the gold tethered peptides had an excellent long-term stability during storage and reuse, with activity remaining stable for at least 7 months. The high stability presumably arises from two factors: the ability of nanoparticles to firmly maintain the active peptides on their surface and the steric repulsion between the peptides immobilized on the surface, which thereby prevents the aggregation and precipitation of nanoparticles. This behaviour could have important implications from the application point of view, due to the possibility to recycle the conjugates multiple times without losing their potency.

The invention claimed is:

1. A method for the prevention and/or treatment of contamination of a product or a surface by *Listeria monocytogenes*, the method comprising contacting the product or surface with a mixture comprising at least one peptide having sequence VRLIVKVRIWRR (SEQ ID NO: 3), or a salt or solvate thereof.

2. The method according to claim 1, wherein said mixture further comprises at least one peptide selected from the group consisting of VRLIVAVRIWRR (SEQ ID NO: 1), VRLIVAVRIKRR (SEQ ID NO: 2), and VRLIVKVRIKRR (SEQ ID NO: 4), or a salt or solvate thereof.

3. The method according to claim 1, wherein said mixture further comprises at least one peptide selected from the group consisting of VRLIVAVRIWRR (SEQ ID NO: 1) and VRLIVAVRIKRR (SEQ ID NO: 2) and at least one peptide having sequence VRLIVKVRIKRR (SEQ ID NO: 4), or a salt or solvate thereof.

4. The method according to claim 1, wherein said mixture is not in association with other bactericidal compounds.

5. The method according to claim 1, wherein said product is a food, a material, or an object.

6. The method according to claim 1, wherein said mixture is applied as a coating composition on said product or surface or linked with a covalent bond to said product or surface.

7. The method according to claim 1, wherein said at least one peptide having sequence VRLIVKVRIWRR (SEQ ID NO: 3) is linked to the surface of nanoparticles.

8. The method according to claim 1, wherein said *Listeria monocytogenes* is an antibiotic-resistant *Listeria monocytogenes* serotype.

9. A method for the treatment of an infection from *Listeria monocytogenes* in a subject in need thereof, said method comprising administering a mixture comprising at least one peptide having sequence VRLIVKVRIWRR (SEQ ID NO: 3) or a pharmaceutically acceptable salt or solvate thereof.

10. The method according to claim 9, wherein said *Listeria monocytogenes* is an antibiotic-resistant *Listeria monocytogenes* serotype.

11. The method according to claim 9, wherein said mixture further comprises at least one peptide selected from the group consisting of VRLIVAVRIWRR (SEQ ID NO: 1), VRLIVAVRIKRR (SEQ ID NO: 2) and VRLIVKVRIKRR (SEQ ID NO: 4), or a pharmaceutically acceptable salt or solvate thereof.

12. The method according to claim 10, wherein said at least one peptide having sequence VRLIVKVRIWRR (SEQ ID NO: 3) is covalently linked to the surface of nanoparticles.

* * * * *

```
SEQUENCE LISTING

Sequence total quantity: 4
SEQ ID NO: 1          moltype = AA  length = 12
FEATURE               Location/Qualifiers
REGION                1..12
                      note = synthetic
source                1..12
                      mol_type = protein
                      organism = unidentified
SEQUENCE: 1
VRLIVAVRIW RR                                                           12

SEQ ID NO: 2          moltype = AA  length = 12
FEATURE               Location/Qualifiers
REGION                1..12
                      note = synthetic
source                1..12
                      mol_type = protein
                      organism = unidentified
SEQUENCE: 2
VRLIVAVRIK RR                                                           12

SEQ ID NO: 3          moltype = AA  length = 12
FEATURE               Location/Qualifiers
REGION                1..12
                      note = synthetic
source                1..12
                      mol_type = protein
                      organism = unidentified
SEQUENCE: 3
VRLIVKVRIW RR                                                           12

SEQ ID NO: 4          moltype = AA  length = 12
FEATURE               Location/Qualifiers
REGION                1..12
                      note = synthetic
source                1..12
                      mol_type = protein
                      organism = unidentified
SEQUENCE: 4
VRLIVKVRIK RR                                                           12
```